US011022608B2

(12) United States Patent
Ferrell et al.

(10) Patent No.: US 11,022,608 B2
(45) Date of Patent: *Jun. 1, 2021

(54) COMPOSITIONS AND METHODS FOR DETECTING AND TREATING PATHOLOGICAL FIBROBLAST CELLS

(71) Applicant: Duke University, Durham, NC (US)

(72) Inventors: Paul Ferrell, Durham, NC (US); Salvatore Pizzo, Durham, NC (US); Robin Bachelder, Durham, NC (US)

(73) Assignee: Duke University, Durham, NC (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/586,532

(22) Filed: Sep. 27, 2019

(65) Prior Publication Data

US 2020/0103397 A1 Apr. 2, 2020

Related U.S. Application Data

(60) Provisional application No. 62/737,167, filed on Sep. 27, 2018.

(51) Int. Cl.
| | |
|---|---|
| *G01N 33/50* | (2006.01) |
| *C12Q 1/6881* | (2018.01) |
| *C07K 16/28* | (2006.01) |
| *A61K 39/395* | (2006.01) |
| *A61P 11/00* | (2006.01) |
| *A61K 45/06* | (2006.01) |

(52) U.S. Cl.
CPC ..... *G01N 33/5091* (2013.01); *A61K 39/3955* (2013.01); *A61K 45/06* (2013.01); *A61P 11/00* (2018.01); *C07K 16/2896* (2013.01); *C12Q 1/6881* (2013.01); *C12Q 2600/158* (2013.01); *G01N 2800/10* (2013.01); *G01N 2800/12* (2013.01)

(58) Field of Classification Search
CPC ........... G01N 33/5091; G01N 2800/12; G01N 2800/10; A61P 11/00; A61K 45/06; A61K 39/3955; C07K 16/2896; C12Q 1/6881; C12Q 2699/158

See application file for complete search history.

(56) References Cited

U.S. PATENT DOCUMENTS

2015/0050240 A1* 2/2015 Rumenova Konstantinova .......... A61K 39/0005
424/85.4

FOREIGN PATENT DOCUMENTS

WO WO-2009055937 A1 * 5/2009 ..... C12Y 304/21075

OTHER PUBLICATIONS

Koch et al., "Structure of the Neural (N-) Cadherin Prodomain Reveals a Cadherin Extracellular Domain-like Fold without Adhesive Characteristics", May 2004, Elsevier Science Ltd., Structure, vol. 12, 793-805 (Year: 2004).*

Human N-Cadherin Propeptide PE-conjugated Antibody Product Datasheet, Feb. 6, 2018, R&D Systems, Catalog No. IC1388P (Year: 2018).*
Human N-Cadherin Propeptide Antibody Antigen Affinity-purified Polyclonal Sheep IgG, Feb. 6, 2018, R&D Systems, Catalog No. AF1388 (Year: 2018).*
Asmani, M., et al., Fibrotic microtissue array to predict anti-fibrosis drug efficacy. Nat Commun. May 25, 2018;9(1):2066.
Caron, P.C., et al., Murine and humanized constructs of monoclonal antibody M195 (anti-CD33) for the therapy of acute myelogenous leukemia. Cancer, 1994. 73(S3): p. 1049-1056.
Daba, et al., Drug-induced Pulmonary Fibrosis. Saudi Med J. Jun. 2004;25(6):700-6.
Elrick, L.J., et al., Generation of a monoclonal human single chain antibody fragment to hepatic stellate cells—a potential mechanism for targeting liver anti-fibrotic therapeutics. J Hepatol. Jun. 2005;42(6):888-96.
Habiel, D.M., et al., Modeling idiopathic pulmonary fibrosis in humanized severe combined immunodeficient mice. The American journal of pathology, 2018. 188(4): p. 891-903.
Hmiel, L.K., et al, Post-translational structural modifications of immunoglobulin G and their effect on biological activity. Analytical and bioanalytical chemistry, 2015. 407(1): p. 79-94.
Maret, D., et al., Surface expression of precursor N-cadherin promotes tumor cell invasion. Neoplasia, 2010. 12(12): p. 1066-1080.
Nelson, E.R., et al., Chemotherapy enriches for an invasive triple-negative breast tumor cell subpopulation expressing a precursor form of N-cadherin on the cell surface. Oncotarget, 2016. 7(51): p. 84030.
Ozawa, M. and R. Kemler, Correct proteolytic cleavage is required for the cell adhesive function of uvomorulin. The Journal of Cell Biology, 1990. 111(4): p. 1645-1650.
Poelstra, K. and D. Schuppan, Targeted therapy of liver fibrosis/cirrhosis and its complications. Journal of hepatology, 2011. 55(3): p. 726-728.
Rockey, D.C., P.D. Bell, and J.A. Hill, Fibrosis—a common pathway to organ injury and failure. New England Journal of Medicine, 2015. 372(12): p. 1138-1149.
Taborda, C.P., et al., More is not necessarily better: prozone-like effects in passive immunization with IgG. The Journal of Immunology, 2003. 170(7): p. 3621-3630.
Wahl, J.K., et al., N-cadherin-catenin complexes form prior to cleavage of the proregion and transport to the plasma membrane. Journal of Biological Chemistry, 2003. 278(19): p. 17269-17276.

(Continued)

*Primary Examiner* — Joanne Hama
*Assistant Examiner* — Scott T. Humbarger
(74) *Attorney, Agent, or Firm* — Casimir Jones, SC; Robert A. Goetz

(57) ABSTRACT

Compositions, kits and methods for assessing the presence of pathological fibroblasts within a biological sample are provided. In addition, compositions, kits and methods for detecting fibrosis are provided. Also provided are methods for treating fibrosis and conditions characterized with pathological fibroblasts.

8 Claims, 13 Drawing Sheets
(8 of 13 Drawing Sheet(s) Filed in Color)
Specification includes a Sequence Listing.

(56) References Cited

OTHER PUBLICATIONS

Wynn, et al., Mechanisms of Fibrosis: Therapeutic Translation for Fibrotic Disease. Nat Med. Jul. 6, 2012;18(7):1028-40.
Wynn, T., Cellular and molecular mechanisms of fibrosis. J Pathol. Jan. 2008;214(2):199-210.
Wynn, T.A., Fibrotic disease and the T H 1/T H 2 paradigm. Nature Reviews Immunology, 2004. 4(8): p. 583.

\* cited by examiner

FIG. 1D. Normal Cardiac Atria Tissue, Pro-N-cadherin IHC

FIG. 1E Fatty Liver Tissue, Pro-N-cadherin IHC
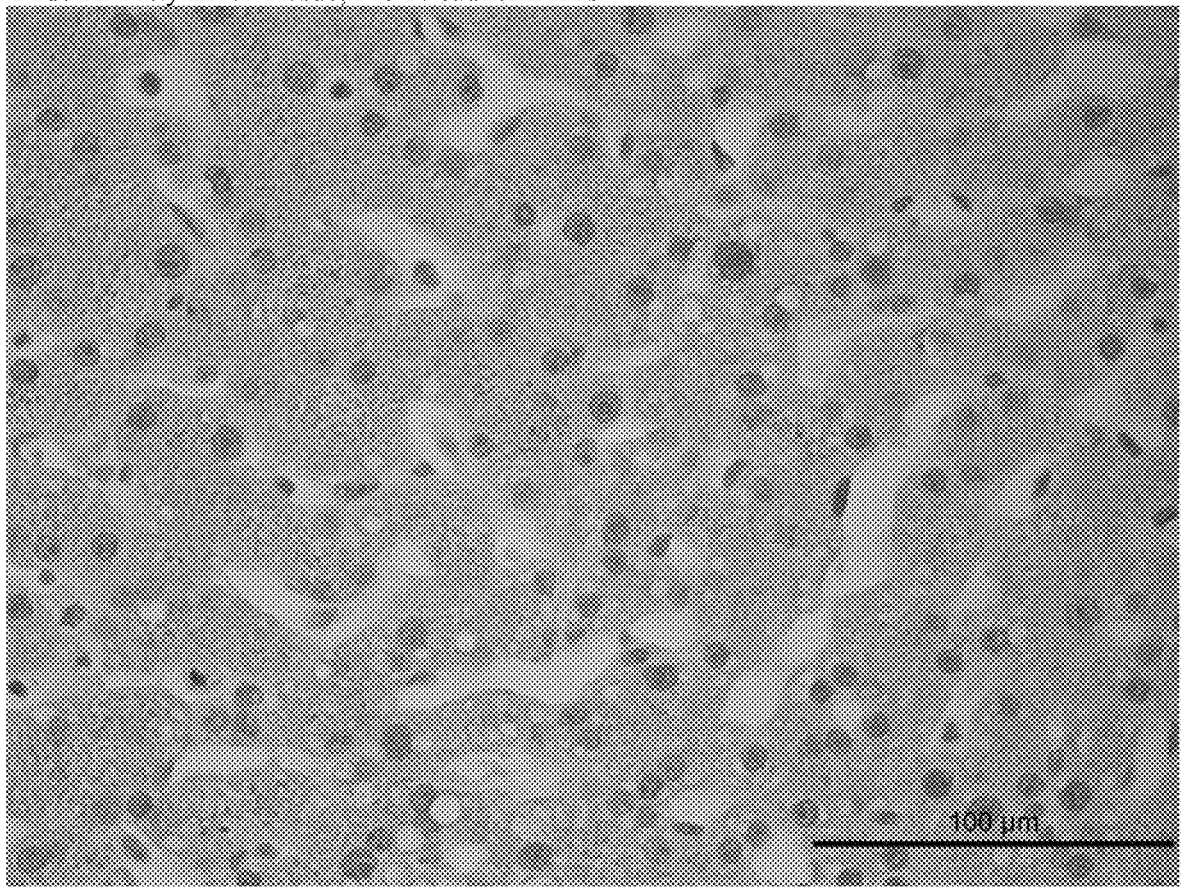
FIG. 1F Dilated Cardiacmyopathy Tissue, Pro-N-cadherin IHC
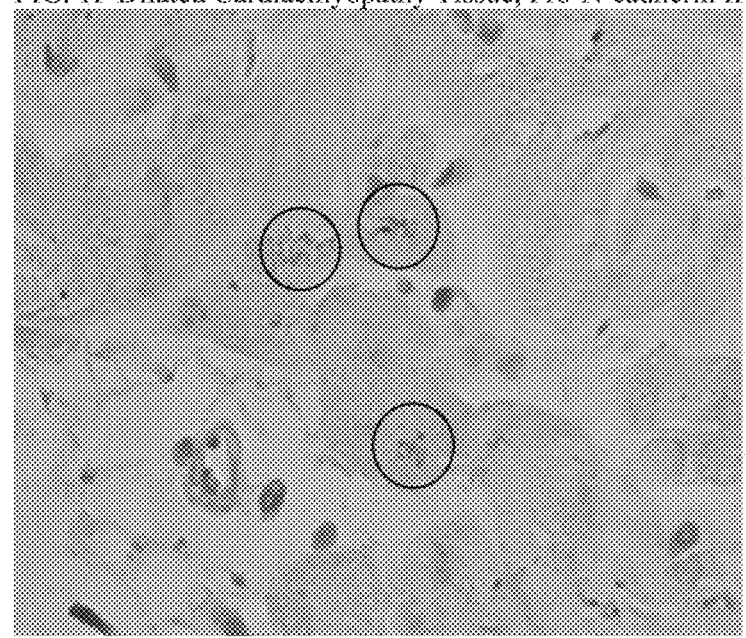

Pro-N-Cadherin MAb is Cytotoxic to Fibroblast Isolated from Idiopathic Pulmonary Fibrosis LL97A Immunostaining (Green – Pro-N-cadherin, Red – Actin Cytoskeleton, Blue – Nuclei)

LL97A Immunostaining (Green – Pro-N-cadherin, Red – Actin Cytoskeleton, Blue – Nuclei)

LL97A Immunostaining (Green – Pro-N-cadherin, Red – Actin Cytoskeleton, Blue – Nuclei)

Permeabilzation of Idiopathic Pulmonary Fibrosis Fibroblast LL97A

SEQUENCE LISTING

```
<160> NUMBER OF SEQ ID NOS: 1

<210> SEQ ID NO 1
<211> LENGTH: 159
<212> TYPE: PRT
<213> ORGANISM: Artificial sequence
<220> FEATURE:
<223> OTHER INFORMATION: synthetic

<400> SEQUENCE: 1

Met Cys Arg Ile Ala Gly Ala Leu Arg Thr Leu Leu Pro Leu Leu Ala
1               5                   10                  15

Ala Leu Leu Gln Ala Ser Val Glu Ala Ser Gly Glu Ile Ala Leu Cys
            20                  25                  30

Lys Thr Gly Phe Pro Glu Asp Val Tyr Ser Ala Val Leu Ser Lys Asp
        35                  40                  45

Val His Glu Gly Gln Pro Leu Leu Asn Val Lys Phe Ser Asn Cys Asn
    50                  55                  60

Gly Lys Arg Lys Val Gln Tyr Glu Ser Ser Glu Pro Ala Asp Phe Lys
65                  70                  75                  80

Val Asp Glu Asp Gly Met Val Tyr Ala Val Arg Ser Phe Pro Leu Ser
                85                  90                  95

Ser Glu His Ala Lys Phe Leu Ile Tyr Ala Gln Asp Lys Glu Thr Gln
            100                 105                 110

Glu Lys Trp Gln Val Ala Val Lys Leu Ser Leu Lys Pro Thr Leu Thr
        115                 120                 125

Glu Glu Ser Val Lys Glu Ser Ala Glu Val Glu Glu Ile Val Phe Pro
    130                 135                 140

Arg Gln Phe Ser Lys His Ser Gly His Leu Gln Arg Gln Lys Arg
145                 150                 155
```

COMPOSITIONS AND METHODS FOR DETECTING AND TREATING PATHOLOGICAL FIBROBLAST CELLS

Under the provisions of the Budapest Treaty on the International Recognition of the Deposit of Microorganisms for the Purpose of Patent Procedure, Applicant has deposited biological material comprising 25 vials of 2-8 million cells of 10A10 hybridoma cells with the International Depositary Authority Patent Depository ATCC, 10801 University Blvd, Manassas, VA 20110 U.S., on Apr. 23, 2021 under the accession number PTA-127069.

FIELD OF THE INVENTION

Compositions, kits and methods for assessing the presence of pathological fibroblasts within a biological sample are provided. In addition, compositions, kits and methods for detecting fibrosis are provided. Also provided are methods for treating fibrosis and conditions characterized with pathological fibroblasts.

INTRODUCTION

Fibrosis is the formation of excess fibrous tissue in an organ or tissue, often as a reaction to inflammation or tissue injury. Pathological fibrosis is characterized by non-resolving or progressive tissue remodeling, which itself can cause tissue damage and organ failure.

Pathological fibroblasts are the drivers of many disease types, fibrosis being the salient feature. The primary hallmark of fibrosis is the chronic and excessive deposition of extracellular matrix by pathological fibroblasts and can arise in any organ of the body, ultimately resulting in organ failure. They can manifest after tissue insult or from idiopathic origin and become invasive, proliferative and deleteriously remodel organ tissue. The fibroblast populations in pathological setting arise from a mixed etiology of progenitor cells. Transdifferentiation of epidermal, endothelial, circulating bone marrow stem cells, pericytes and hepatic stellate cells all contribute to the total pool of fibroblasts in pathological setting depending on the effected organ. To date, there is no clear, clinical diagnostic marker to distinguish healthy, normal fibroblasts from pathological fibroblasts and no effective clinical treatment for the disease they cause such as fibrosis.

As such, there is an urgent need for diagnostic markers distinguishing normal fibroblasts from pathological fibroblasts, and related methods for treating conditions related to such pathological fibroblasts.

The present invention addresses such needs.

SUMMARY OF THE INVENTION

Fibrosis is the aberrant remodeling of tissue architecture which results in loss of function and inevitably organ failure. It can arise in any organ in the body and manifest from many different disease origins; it is the major and only predictable gross physiological feature of many different diseases that is linearly correlated to organ failure. It is a biologically conserved process regardless of the organ of origin and common endpoint regardless of insult (see, Rockey, D. C., P. D. Bell, and J. A. Hill, New England Journal of Medicine, 2015. 372(12): p. 1138-1149). In the United States, 45% of all deaths can be attributed to some kind of chronic fibrotic related disease (see, Wynn, T., The Journal of Pathology: A Journal of the Pathological Society of Great Britain and Ireland, 2008. 214(2): p. 199-210; Wynn, T. A., Nature Reviews Immunology, 2004. 4(8): p. 583). Collectively, fibrotic disease kills more people than cancer.

The current scientific theory describes fibrosis as the pathological and constitutive activation state of fibroblasts which result in excessive extracellular matrix turnover and deposition that interferes with normal organ function. Currently, an activated state of these fibroblasts is defined by their acquisition of alpha-smooth muscle actin ($\alpha$-SMA) protein. Fibroblasts expressing this protein are defined as myofibroblasts, which are an extremely active, synthetic, tissue remodeling cell type. However, a true disease specific marker for these cells does not currently exist. Experiments conducted herein identified a biomarker on a subpopulation of myofibroblasts that exists only in pathological settings due to defective cellular processing and subsequent localization of the aberrantly processed isoform of N-cadherin to the cell surface. This biomarker, Pro-N-Cadherin, can distinguish a pathological fibroblast population from surrounding fibroblasts. Consistently, this novel biomarker of pathological fibroblasts has been found on the cell surface of patient derived myofibroblasts isolated from dilated cardiac myopathy, idiopathic pulmonary fibrosis, and the most well characterized hepatic stellate, myofibroblast cell line LX2, used for studying liver cirrhosis. Importantly, this N-cadherin isoform, Pro-N-cadherin, is not expressed on non-pathologic fibroblasts or myofibroblasts found in normal tissue.

Due to an error in protein processing and subsequent localization, Pro-N-cadherin is expressed on the cell surface of a subpopulation of myofibroblasts derived from several pathological settings of fibrosis, but not on myofibroblasts derived from physiologically normal tissues or on any other normal cell types. Pro-N-cadherin is the precursor form of the protein N-cadherin. Pro-N-cadherin is normally processed inside the Golgi apparatus by furin proteases to produce the mature protein N-cadherin, where the pro domain is removed from the protein prior to being transported to the cell surface to serve as a cell adhesion molecule (see, Ozawa, M. and R. Kemler, The Journal of Cell Biology, 1990. 111(4): p. 1645-1650; Wahl, J. K., et al., Journal of Biological Chemistry, 2003. 278(19): p. 17269-17276). However, there have been a few reports published in the cancer literature demonstrating the aberrant cellular localization of pro-N-cadherin on the surface of cancer cells in its immature, unprocessed form (with the Pro portion of the protein still intact) (see, Maret, D., et al., Neoplasia, 2010. 12(12): p. 1066-1080; Nelson, E. R., et al., Oncotarget, 2016. 7(51): p. 84030).

Experiments conducted during the course of developing embodiments for the present invention determined that the precursor for N-cadherin, pro-N-cadherin, is expressed on a pathologic subpopulation of fibroblasts and serves as a diagnostic and therapeutic target to identify and subsequently, inhibit invasion, proliferation, activation and induce cell death of pathological fibroblasts independent of normal, healthy fibroblasts. Such experiments identified this aberrant phenomenon to occur in patient derived tissues and myofibroblasts from fibrosis of the heart, lung and liver. Such experiments also identified a unique monoclonal antibody that, upon binding to pro-N-cadherin on pathologic myofibroblasts, induces cell death in vitro and rapidly eliminates this pathologic myofibroblast subpopulation without effecting fibroblasts or myofibroblasts isolated from normal tissue.

Accordingly, one aspect of the present disclosure provides a method of diagnosing fibrosis or conditions characterized with pathological fibroblasts (e.g., fibroblasts expressing pro-N-cadherin) in a subject comprising, consisting of, or consisting essentially of quantifying the amount of at least one biomarker present in a biological sample derived from the subject, wherein the biomarker is associated with fibrosis or conditions characterized with pathological fibroblasts.

Another aspect of the present disclosure provides a method of determining the presence of fibrosis or pathological fibroblasts (e.g., fibroblasts expressing pro-N-cadherin) in a subject comprising, consisting of, or consisting essentially of: (a) obtaining a biological sample from a subject; (b) determining the expression level of one or more biomarkers that are associated with fibrosis or pathological fibroblasts (e.g., fibroblasts expressing pro-N-cadherin) in the biological sample; (c) comparing the expression level of the biomarker(s) in the biological sample with that of a control, wherein the presence of one or more of the biomarker(s) in the sample that is in an amount greater than that of the control indicates fibrosis or pathological fibroblasts (e.g., fibroblasts expressing pro-N-cadherin); and (d) administering appropriate anti-fibrotic therapy if one or more of the biomarkers are expressed.

Another aspect of the present disclosure provides a method of diagnosing fibrosis or conditions characterized with pathological fibroblasts (e.g., fibroblasts expressing pro-N-cadherin) in a subject comprising, consisting of, or consisting essentially of: (a) obtaining a biological sample from a subject; (b) determining the expression level of one or more biomarkers that are associated with fibrosis in the biological sample; (c) comparing the expression level of the biomarkers in the biological sample with that of a control, wherein the presence of one or more of the biomarkers in the sample that is in an amount greater than that of the control indicates fibrosis or conditions characterized with pathological fibroblasts (e.g., fibroblasts expressing pro-N-cadherin); and (d) administering appropriate anti-fibrotic therapy if one or more of the biomarkers are expressed.

Another aspect of the present disclosure provides methods of prognosing or of aiding prognosis of fibrosis or conditions associated with pathological fibroblast cells (e.g., fibroblasts expressing pro-N-cadherin) are provided. In such embodiments, a biological sample is obtained from the patient and the expression of pro-N-cadherin on fibroblasts measured. In certain embodiments, pro-N-cadherin on fibroblasts is indicative of a prognosis for shortened survival compared to median survival. In such embodiments, reduced expression of pro-N-cadherin on fibroblasts is indicative of a prognosis for increased survival compared to median survival. In such embodiments, expression of pro-N-cadherin on fibroblasts is measured by assaying for mRNA levels. In some embodiments, the assay comprises a PCR method and/or the use of a microarray chip. In one embodiment, the PCR method is qPCR. In one embodiment, the PCR method is multiplex-PCR. In such embodiments, expression of pro-N-cadherin on fibroblasts is measured through use of an antibody specific for pro-N-cadherin.

Such methods are not limited to a particular biomarker associated with fibrosis or conditions associated with pathological fibroblasts (e.g., fibroblasts expressing pro-N-cadherin). In some embodiments, the biomarker is pro-N-Cadherin. In some embodiments, the biomarker comprises fibroblast cells expressing pro-N-Cadherin.

Such methods are not limited to a particular anti-fibrotic therapy. In some embodiments, the anti-fibrotic therapy comprises any agent capable of inhibiting expression and/or activity related to pro-N-cadherin expression and/or activity. In some embodiments, the agent capable of inhibiting expression and/or activity related to pro-N-cadherin expression and/or activity is a small molecule, a polypeptide or peptide fragment, an siRNA, or an antibody or fragment thereof.

In some embodiments, the anti-fibrotic therapy includes compounds and compositions designed to stimulate the immune system to specifically recognize antigens expressed or overexpressed such pathological fibroblast cells (e.g., fibroblast cells expressing pro-N-cadherin). Non-limiting examples of antigen-specific immunotherapeutic agents include vaccines (e.g., peptide vaccines), antibodies, cytotoxic T cell lymphocytes (CTLs), chimeric antigen receptor T cells (CAR-T cells), and combinations thereof.

In other embodiments, the antibody comprises an antibody against pro-N-cadherin. In certain embodiments, the antibody comprises a monoclonal antibody (mAb).

In some embodiments, the subject is a mammal. In other embodiments, the subject is a human.

In other embodiments, the biological sample is selected from the group consisting of tissues, cells, biopsies, blood, lymph, serum, plasma, urine, saliva, mucus, and tears. In certain embodiments, the sample comprises biopsies.

In some embodiments, the biological sample comprises fibroblast cells.

In some embodiments, the biological sample comprises lung tissue.

In some embodiments, the biological sample for use according to any of the above methods is lung tissue, whole blood, or serum. In some embodiments, the biological sample is lung tissue or whole blood and the expression of fibroblasts expressing pro-N-cadherin is measured using a PCR method or a microarray chip. In certain embodiments, the biological sample is serum and the expression of fibroblasts expressing pro-N-cadherin is measured using an immunoassay.

Such methods are not limited to a particular manner for measuring the biomarker associated with fibrosis or conditions associated with pathological fibroblasts (e.g., fibroblasts expressing pro-N-cadherin). In some embodiments, the biomarker is measured through use of an antibody specific for fibroblasts expressing pro-N-cadherin. In some embodiments, the biomarker is measured by microarray. In another aspect gene expression of the biomarker (e.g., fibroblasts expressing pro-N-cadherin) is measured by real-time quantitative polymerase chain reaction (qPCR). In another aspect, gene expression is measured by multiplex-PCR. According to another embodiment, gene expression is measured by observing protein expression levels of fibroblasts expressing pro-N-cadherin. According to another embodiment, expression of pro-N-cadherin within fibroblast cells is considered elevated when compared to a healthy control or a reference subject if the relative mRNA level is greater than 2 fold of the level of a control or reference gene mRNA. According to another embodiment, the relative mRNA level is greater than 3 fold, fold, 10 fold, 15 fold, 20 fold, 25 fold, or 30 fold compared to a healthy control or reference gene expression level. In one aspect, the gene expression level is measured by a method selected from a PCR method, a microarray method, or an immunoassay method. In one embodiment, the microarray method comprises the use of a microarray chip having one or more nucleic acid molecules that can hybridize under stringent conditions to a nucleic acid molecule encoding fibroblasts expressing pro-N-cadherin or having one or more polypeptides (such as peptides or antibodies) that can bind to fibroblasts expressing pro-N-cadherin. In one embodiment, the PCR method is qPCR. In one embodiment, the PCR method is multiplex-PCR. According to one embodiment, the immunoassay method comprises binding an antibody to pro-N-cadherin expressed within fibroblast cells in a patient sample and determining if the level from the patient sample is elevated. In certain embodiments, the immunoassay method is an enzyme-linked immunosorbent assay (ELISA).

Such methods are not limited to a particular condition associated with pathological fibroblasts.

In some embodiments, the conditions characterized with pathological fibroblasts are selected from fibrotic liver disease, hepatic ischemia-reperfusion injury, cerebral infarction, ischemic heart disease, cardiac fibrosis, renal disease or lung (pulmonary) fibrosis. In other embodiments, the disease or condition is liver fibrosis associated with hepatitis C, hepatitis B, delta hepatitis, chronic alcoholism, non-alcoholic steatohepatitis, extrahepatic obstructions (stones in the bile duct), cholangiopathies (primary biliary cirrhosis and sclerosing cholangitis), autoimmune liver disease, and inherited metabolic disorders (Wilson's disease, hemochromatosis, and alpha-1 antitrypsin deficiency); damaged and/or ischemic organs, transplants or grafts; ischemia/reperfusion injury; stroke; cerebrovascular disease; myocardial ischemia; atherosclerosis; pancreatitis; renal failure; renal fibrosis; scleroderma; systemic sclerosis; dermal fibrosis and idiopathic pulmonary fibrosis. In still further embodiments, the treatment is for wounds for acceleration of healing; reducing post-surgical scarring; reducing adhesion formation; vascularization of a damaged and/or ischemic organ, transplant or graft; amelioration of ischemia/reperfusion injury in the brain, heart, liver, kidney, and other tissues and organs; normalization of myocardial perfusion as a consequence of chronic cardiac ischemia or myocardial infarction; development or augmentation of collateral vessel development after vascular occlusion or to ischemic tissues or organs; fibrotic diseases; hepatic disease including fibrosis and cirrhosis; lung fibrosis; radiocontrast nephropathy; fibrosis secondary to renal obstruction; renal trauma and transplantation; renal failure secondary to chronic diabetes and/or hypertension; muscular dystrophy, amyotrophic lateral sclerosis, and/or diabetes mellitus.

In certain embodiments, subjects characterized as having fibrosis or conditions associated with pathological fibroblasts (e.g., fibroblast cells expressing pro-N-cadherin) are further administered one or more additional therapeutic agents. For example, in some embodiments, the additional therapeutic agent is selected from an anti-IL-13 agent, an anti-IL-4 agent, a combination anti-IL-13/anti-IL-4 agent, pirfenidone, anti-LOXL2 antibody (GS-6624), N-acetylcysteine, anti-TGF-.beta. antibody (GC1008), anti-.alpha.v-.beta.6 integrin antibody (STX-100), anti-CTGF antibody (FG-3019), anti-CCL2 antibody (CNTO 888), somatostatin analog (SOM230, octreotide), antiotensin II inhibitor (losartan), carbon monoxide, thalidomide, tetrathiomolybdate, doxycycline, minocycline, and tyrosine kinase inhibitor (BIBF1120).

Yet another aspect of the present disclosure provides a method of treating and/or preventing fibrosis in a subject, the method comprising, consisting of, or consisting essentially of administering to the subject a therapeutically effective amount of a Pro-N-Cadherin inhibiting molecule such that the fibrosis is treated in the subject.

In some embodiments, the Pro-N-Cadherin inhibiting molecule is selected from the group consisting of a small molecule, an antibody, a miRNA, an antisense RNA, an oligonucleotide, aptamers, siRNA, peptides, polypeptides and combinations thereof.

In some embodiments, the inhibiting molecule comprises an antibody. In one embodiment, the antibody comprises a monoclonal antibody. In one embodiment, the antibody comprises 10A10.

The invention also provides kits comprising an antibody specific for fibroblasts expressing pro-N-cadherin and instructions for administering the compound to an animal. The kits may optionally contain other therapeutic agents, e.g., agents useful in treating fibrosis or conditions associated with pathological fibroblasts (e.g., fibroblasts expressing pro-N-cadherin).

BRIEF DESCRIPTION OF THE DRAWINGS

The patent or application file contains at least one drawing executed in color. Copies of this patent or patent application publication with color drawings will be provided by the Office upon request and payment of the necessary fee.

FIG. 1A-F: Pro-N-cadherin mAb reacts specifically with the pro domain of pro-N-cadherin from pathological myofibroblasts but not non-pathological. A. Fibroblasts and myofibroblasts from various origins were stained and analyzed by flow cytometry using pro-N-cadherin mAb (5 ug/mL), excluding dead cells via gating and 7AAD exclusion on Flowjo analysis software. Cell surface pro-N-cadherin positivity was found on myofibroblasts from pathological origins LL97A, CF-DCM, and LX2. Representative data of cardiac myofibroblasts from dilated cardiomyopathy (CF-DCM) was generated from myofibroblasts isolated from two separate explant patient hearts from DUMC. Pro-N-cadherin was not detected on primary normal human lung fibroblasts (NHLF), primary normal human cardiac fibroblasts (NHCF), or immortalized CCD-16Lu myofibroblast cell line from healthy donor. Mouse IgG control (red histogram) relative to pro-n-cadherin mAb (blue histogram). B. Total protein lysates were analyzed by western blot for each cell line and corroborates pro-N-cadherin cell surface data. C. IHC performed for pro-N-cadherin was positive in patient tissue received from cirrhotic liver but not normal liver. D. IHC of normal human atrial tissue trimmings from implanted heart (with 10A10 pro-N-cadherin antibody). E. IHC of fatty liver tissue (with 10A10 pro-N-cadherin antibody). F. IHC of heart-dilated cardiomyopathy, focus: Interstitial fibroblasts (with 10A10 pro-N-cadherin antibody).

Figure 4:
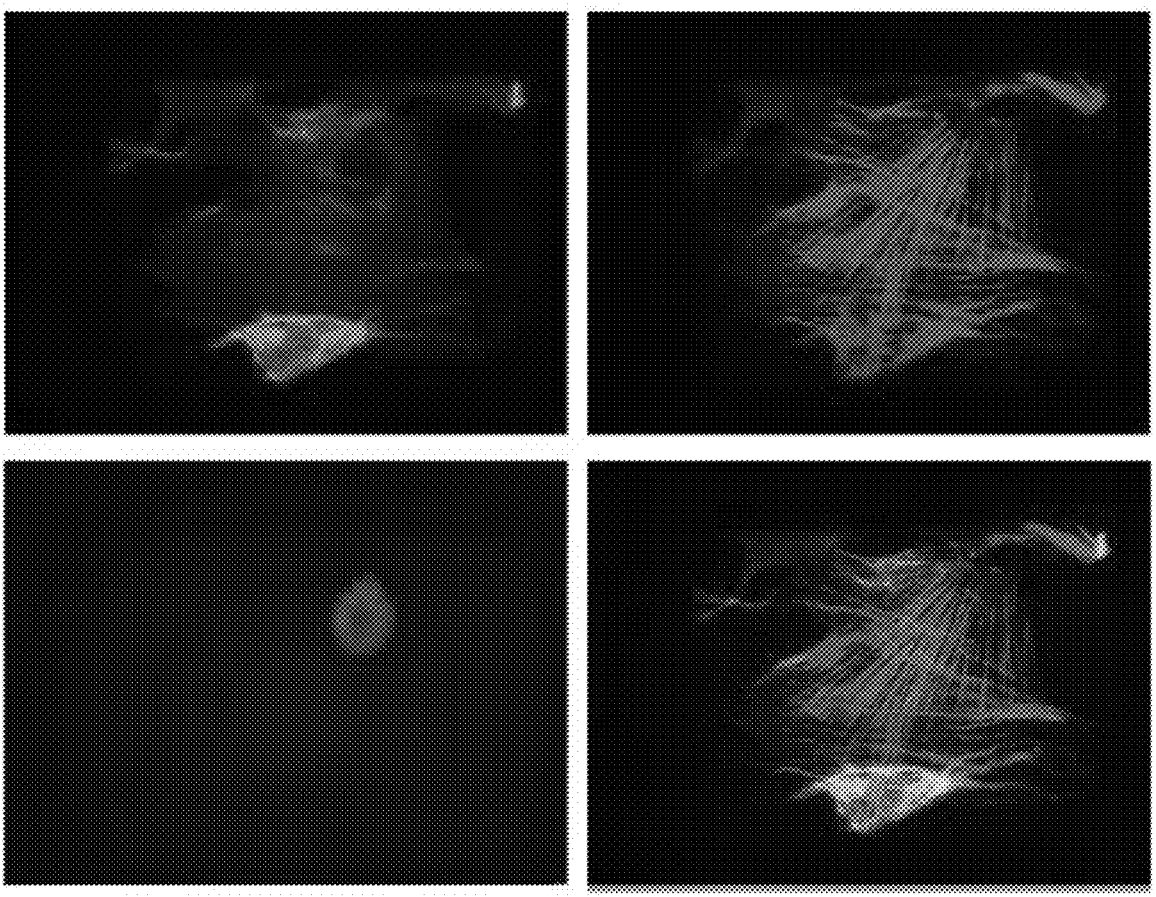
Figure 5:
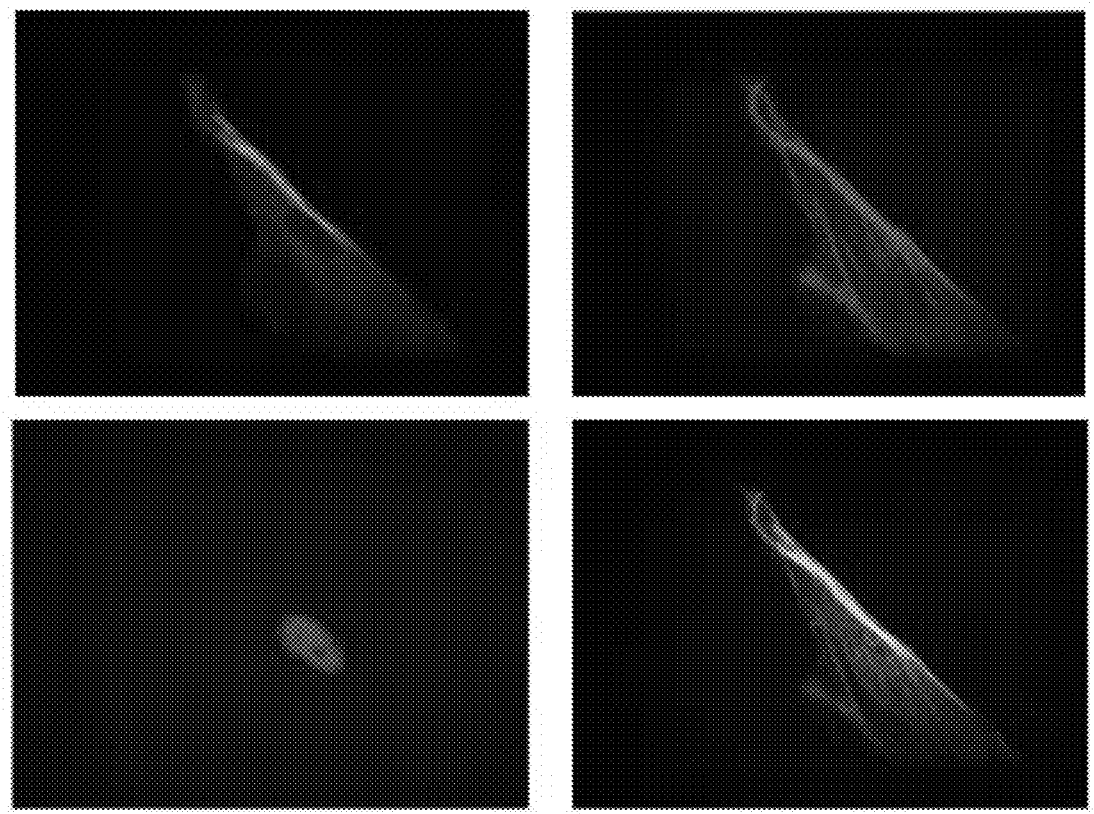
Figure 6:
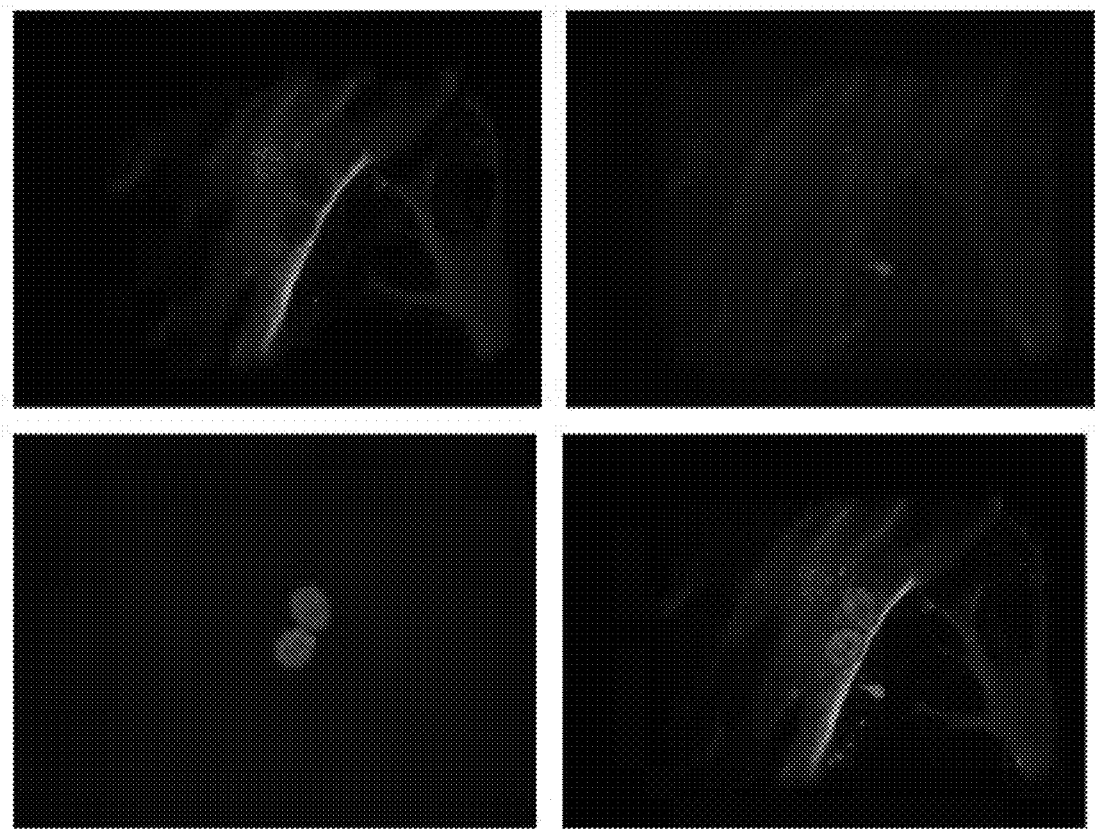

FIGS. 4, 5, 6: LL97A Immunostaining. Images showing fibroblast cells expressing pro-N-cadherin (Green—Pro-N-cadherin; Red—Actin Cytoskeleton; Blue—Nuclei; Yellow—Actin/Pro-N-cadherin colocalization).

Figure 7:
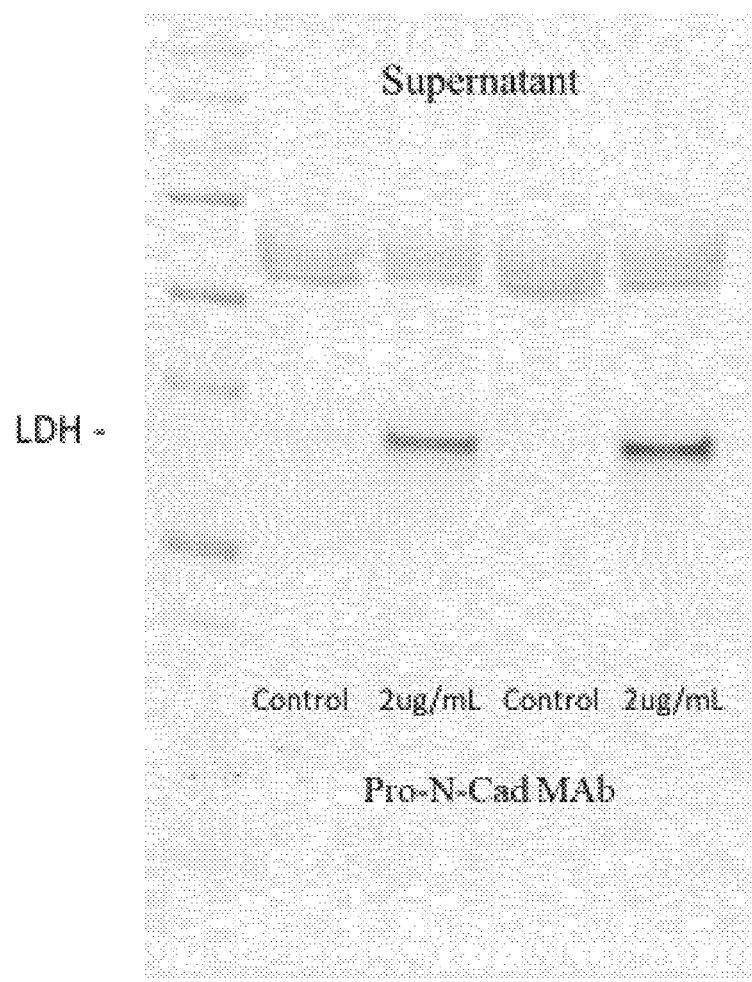

FIG. 7: Permeabilzation of Idiopathic Pulmonary Fibrosis Fibroblast LL97A. LL97A cells were plated at $5\times10^4$ cells/well in a 6-well plate and allowed to anchor overnight. The following day, the media was replaced with serum free media. Cells were treated with Pro-N-cadherin antibody 10A10 for 4 hours, supernatant was removed and concentrated, and analyzed by western blot. Membrane was probed with LDH antibody.

DEFINITIONS

Unless otherwise defined, all terms of art, notations and other scientific terminology used herein are intended to have the meanings commonly understood by those of skill in the art to which this invention pertains. In some cases, terms with commonly understood meanings are defined herein for clarity and/or for ready reference, and the inclusion of such definitions herein should not necessarily be construed to represent a substantial difference over what is generally understood in the art. The techniques and procedures described or referenced herein are generally well understood and commonly employed using conventional methodology by those skilled in the art, such as, for example, the widely utilized molecular cloning methodologies described in Sambrook et al., Molecular Cloning: A Laboratory Manual 2nd. edition (1989) Cold Spring Harbor Laboratory Press, Cold Spring Harbor, N.Y. As appropriate, procedures involving the use of commercially available kits and reagents are generally carried out in accordance with manufacturer defined protocols and/or parameters unless otherwise noted.

Articles "a" and "an" are used herein to refer to one or to more than one (i.e. at least one) of the grammatical object of the article. By way of example, "an element" means at least one element and can include more than one element.

"About" is used to provide flexibility to a numerical range endpoint by providing that a given value may be "slightly above" or "slightly below" the endpoint without affecting the desired result.

The use herein of the terms "including," "comprising," or "having," and variations thereof, is meant to encompass the elements listed thereafter and equivalents thereof as well as additional elements. Embodiments recited as "including," "comprising," or "having" certain elements are also contemplated as "consisting essentially of" and "consisting of" those certain elements. As used herein, "and/or" refers to and encompasses any and all possible combinations of one or more of the associated listed items, as well as the lack of combinations where interpreted in the alternative ("or").

As used herein, the transitional phrase "consisting essentially of" (and grammatical variants) is to be interpreted as encompassing the recited materials or steps "and those that do not materially affect the basic and novel characteristic(s)" of the claimed invention. See, In re Herz, 537 F.2d 549, 551-52, 190 U.S.P.Q. 461, 463 (CCPA 1976) (emphasis in the original); see also MPEP § 2111.03. Thus, the term "consisting essentially of" as used herein should not be interpreted as equivalent to "comprising."

Moreover, the present disclosure also contemplates that in some embodiments, any feature or combination of features set forth herein can be excluded or omitted. To illustrate, if the specification states that a complex comprises components A, B and C, it is specifically intended that any of A, B or C, or a combination thereof, can be omitted and disclaimed singularly or in any combination.

Recitation of ranges of values herein are merely intended to serve as a shorthand method of referring individually to each separate value falling within the range, unless otherwise-Indicated herein, and each separate value is incorporated into the specification as if it were individually recited herein. For example, if a concentration range is stated as 1% to 50%, it is intended that values such as 2% to 40%, 10% to 30%, or 1% to 3%, etc., are expressly enumerated in this specification. These are only examples of what is specifically intended, and all possible combinations of numerical values between and including the lowest value and the highest value enumerated are to be considered to be expressly stated in this disclosure.

Unless otherwise defined, all technical terms used herein have the same meaning as commonly understood by one of ordinary skill in the art to which this disclosure belongs.

As used herein, the term "biomarker" refers to a naturally occurring biological molecule present in a subject at varying concentrations useful in predicting the risk or incidence of a disease or a condition, such as fibrosis. For example, the biomarker can be a protein present in higher or lower amounts in a subject at risk for fibrosis. The biomarker can include nucleic acids, ribonucleic acids, or a polypeptide used as an indicator or marker for fibrosis in the subject. In some embodiments, the biomarker comprises a protein. A biomarker may also comprise any naturally or non-naturally occurring polymorphism (e.g., single-nucleotide polymorphism [SNP]) present in a subject that is useful in predicting the risk or incidence of fibrosis. In certain embodiments, the biomarker comprises Pro-N-Cadherin. In certain embodiments, the biomarker comprises fibroblasts expressing pro-N-Cadherin.

As used herein, "fibrosis" refers to the formation of excess fibrous connective tissue as a result of the excess deposition of extracellular matrix components, for example collagen. Fibrous connective tissue is characterized by having extracellular matrix (ECM) with a high collagen content. The collagen may be provided in strands or fibers, which may be arranged irregularly or aligned. The ECM of fibrous connective tissue may also include glycosaminoglycans.

As used herein, "excess fibrous connective tissue" refers to an amount of connective tissue at a given location (e.g. a given tissue or organ, or part of a given tissue or organ) which is greater than the amount of connective tissue present at that location in the absence of fibrosis, e.g. under normal, non-pathological conditions. As used herein, "excess deposition of extracellular matrix components" refers to a level of deposition of one or more extracellular matrix components which is greater than the level of deposition in the absence of fibrosis, e.g. under normal, non-pathological conditions.

As used herein, the term "disease" refers to any abnormal condition and/or disorder of a structure or a function that affects a part of an organism. It may be caused by an external factor, such as an infectious disease, or by internal dysfunctions, such as fibrosis and the like.

As used herein, the term "fibrosis" also refers to those diseases/conditions associated with, or characterized by, fibrosis. Examples include, but are not limited to, respiratory conditions such as pulmonary fibrosis, cystic fibrosis, idiopathic pulmonary fibrosis, progressive massive fibrosis, scleroderma, obliterative bronchiolitis, Hermansky-Pudlak syndrome, asbestosis, silicosis, chronic pulmonary hypertension, AIDS associated pulmonary hypertension, sarcoidosis, tumor stroma in lung disease, and asthma; chronic liver disease, primary biliary cirrhosis (PBC), schistosomal liver disease, liver cirrhosis; cardiovascular conditions such as hypertrophic cardiomyopathy, dilated cardiomyopathy (DCM), fibrosis of the atrium, atrial fibrillation, fibrosis of the ventricle, ventricular fibrillation, myocardial fibrosis, Brugada syndrome, myocarditis, endomyocardial fibrosis, myocardial infarction, fibrotic vascular disease, hypertensive heart disease, arrhythmogenic right ventricular cardiomyopathy (ARVC), tubulointerstitial and glomerular fibrosis, atherosclerosis, varicose veins, cerebral infarcts; neurological conditions such as gliosis and Alzheimer's disease; muscular dystrophy such as Duchenne muscular dystrophy (DMD) or Becker's muscular dystrophy (BMD); gastrointestinal conditions such as Chron's disease, microscopic colitis and primary sclerosing cholangitis (PSC); skin conditions such as scleroderma, nephrogenic systemic fibrosis and cutis keloid; arthrofibrosis; Dupuytren's contracture; mediastinal fibrosis; retroperitoneal fibrosis; myelofibrosis; Peyronie's disease; adhesive capsulitis; kidney disease (e.g., renal fibrosis, nephritic syndrome, Alport's syndrome, HIV associated nephropathy, polycystic kidney disease, Fabry's disease, diabetic nephropathy, chronic glomerulonephritis, nephritis associated with systemic lupus); progressive systemic sclerosis (PSS); chronic graft versus host disease; diseases of the eye such as Grave's ophthalmopathy, epiretinal fibrosis, retinal fibrosis, subretinal fibrosis (e.g. associated with macular degeneration (e.g. wet age-related macular degeneration (AMD)), diabetic retinopathy, glaucoma, corneal fibrosis, post-surgical fibrosis (e.g. of the posterior capsule following cataract surgery, or of the bleb following trabeculectomy for glaucoma), conjunctival fibrosis, subconjunctival fibrosis; arthritis; fibrotic pre-neoplastic and fibrotic neoplastic disease; and fibrosis induced by chemical or environmental insult (e.g., cancer chemotherapy, pesticides, radiation/cancer radiotherapy).

DETAILED DESCRIPTION OF THE INVENTION

The cellular and molecular mechanisms of fibrosis are described in Wynn, J. Pathol. (2008) 214(2): 199-210, and Wynn and Ramalingam, Nature Medicine (2012) 18:1028-1040, which are hereby incorporated by reference in their entirety.

The main cellular effectors of fibrosis are myofibroblasts, which produce a collagen-rich extracellular matrix.

In response to tissue injury, damaged cells and leukocytes produce pro-fibrotic factors such as TGF-β, IL-13 and PDGF, which activate fibroblasts to αSMA-expressing myofibroblasts, and recruit myofibroblasts to the site of injury. Myofibroblasts produce a large amount of extracellular matrix, and are important mediators in aiding contracture and closure of the wound. However, under conditions of persistent infection or during chronic inflammation there can be overactivation and recruitment of myofibroblasts, and thus over-production of extracellular matrix components, resulting in the formation of excess fibrous connective tissue.

In some embodiments, fibrosis may be triggered by pathological conditions, e.g. conditions, infections or disease states that lead to production of pro-fibrotic factors such as TGF-β1. In some embodiments, fibrosis may be caused by physical injury/stimuli, chemical injury/stimuli or environmental injury/stimuli. Physical injury/stimuli may occur during surgery, e.g. iatrogenic causes. Chemical injury/stimuli may include drug induced fibrosis, e.g. following chronic administration of drugs such as bleomycin, cyclophosphamide, amiodarone, procainamide, penicillamine, gold and nitrofurantoin (see, e.g., Daba et al., Saudi Med J 2004 June; 25(6): 700-6). Environmental injury/stimuli may include exposure to asbestos fibers or silica.

In embodiments herein, fibrosis may involve an organ of the gastrointestinal system, e.g. of the liver, small intestine, large intestine, or pancreas. In some embodiments, fibrosis may involve an organ of the respiratory system, e.g. the lungs. In embodiments, fibrosis may involve an organ of the cardiovascular system, e.g. of the heart or blood vessels. In some embodiments, fibrosis may involve the skin. In some embodiments, fibrosis may involve an organ of the nervous system, e.g. the brain. In some embodiments, fibrosis may involve an organ of the urinary system, e.g. the kidneys. In some embodiments, fibrosis may involve an organ of the musculoskeletal system, e.g. muscle tissue.

Fibrosis can occur in many tissues of the body. For example, fibrosis can occur in the liver (e.g. cirrhosis), lungs, kidney, heart, blood vessels, eye, skin, pancreas, intestine, brain, and bone marrow. Fibrosis may also occur in multiple organs at once.

Experiments conducted during the course of developing embodiments for the present invention determined that the precursor for N-cadherin, pro-N-cadherin, is expressed on a pathologic subpopulation of fibroblasts and serves as a diagnostic and therapeutic target to identify and subsequently inhibit invasion, proliferation, activation and induce cell death of pathological fibroblasts independent of normal, healthy fibroblasts.

Accordingly, one aspect of the present disclosure provides a method of diagnosing fibrosis or conditions characterized with pathological fibroblasts (e.g., fibroblasts expressing pro-N-cadherin) in a subject comprising, consisting of, or consisting essentially of quantifying the amount of at least one biomarker present in a biological sample derived from the subject, wherein the biomarker is associated with fibrosis or conditions characterized with pathological fibroblasts.

Another aspect of the present disclosure provides a method of determining the presence of fibrosis or pathological fibroblasts (e.g., fibroblasts expressing pro-N-cadherin) in a subject comprising, consisting of, or consisting essentially of: (a) obtaining a biological sample from a subject; (b) determining the expression level of one or more biomarkers that are associated with fibrosis or pathological fibroblasts (e.g., fibroblasts expressing pro-N-cadherin) in the biological sample; (c) comparing the expression level of the biomarker(s) in the biological sample with that of a control, wherein the presence of one or more of the biomarker(s) in the sample that is in an amount greater than that of the control indicates fibrosis or pathological fibroblasts (e.g., fibroblasts expressing pro-N-cadherin); and (d) administering appropriate anti-fibrotic therapy if one or more of the biomarkers are expressed.

Another aspect of the present disclosure provides a method of diagnosing fibrosis or conditions characterized with pathological fibroblasts (e.g., fibroblasts expressing pro-N-cadherin) in a subject comprising, consisting of, or consisting essentially of: (a) obtaining a biological sample from a subject; (b) determining the expression level of one or more biomarkers that are associated with fibrosis in the biological sample; (c) comparing the expression level of the biomarkers in the biological sample with that of a control, wherein the presence of one or more of the biomarkers in the sample that is in an amount greater than that of the control indicates fibrosis or conditions characterized with pathological fibroblasts (e.g., fibroblasts expressing pro-N-cadherin); and (d) administering appropriate anti-fibrotic therapy if one or more of the biomarkers are expressed.

Another aspect of the present disclosure provides methods of prognosing or of aiding prognosis of fibrosis or conditions associated with pathological fibroblast cells (e.g., fibroblasts expressing pro-N-cadherin) are provided. In such embodiments, a biological sample is obtained from the patient and the expression of pro-N-cadherin on fibroblasts measured. In certain embodiments, pro-N-cadherin on fibroblasts is indicative of a prognosis for shortened survival compared to median survival. In such embodiments, reduced expression of pro-N-cadherin on fibroblasts is indicative of a prognosis for increased survival compared to median survival. In such embodiments, expression of pro-N-cadherin on fibroblasts is measured by assaying for mRNA levels. In some embodiments, the assay comprises a PCR method and/or the use of a microarray chip. In one embodiment, the PCR method is qPCR. In one embodiment, the PCR method is multiplex-PCR. In such embodiments, expression of pro-N-cadherin on fibroblasts is measured through use of an antibody specific for pro-N-cadherin.

Yet another aspect of the present disclosure provides a method of treating a subject suffering from fibrosis or a condition associated with pathological fibroblast cells (e.g., fibroblasts expressing pro-N-cadherin) comprising, consisting of, or consisting essentially of administering to the subject a therapeutically effective amount of an antibody specific for fibroblasts expressing pro-N-cadherin.

In some embodiments, the antibody can be administered in combination with an anti-fibrotic therapy. Such methods are not limited to a particular anti-fibrotic therapy. In some embodiments, the anti-fibrotic therapy comprises an anti-IL-13 agent, an anti-IL-4 agent, a combination anti-IL-13/anti-IL-4 agent, pirfenidone, anti-LOXL2 antibody (GS-6624), N-acetylcysteine, anti-TGF-.beta. antibody (GC1008), anti-.alpha.v.beta.6 integrin antibody (STX-100), anti-CTGF antibody (FG-3019), anti-CCL2 antibody (CNTO 888), somatostatin analog (SOM230, octreotide), antiotensin II inhibitor (losartan), carbon monoxide, thalidomide, tetrathiomolybdate, doxycycline, minocycline, and tyrosine kinase inhibitor (BIBF1120).

Such methods are not limited to a particular biomarker associated with fibrosis or conditions associated with pathological fibroblasts (e.g., fibroblasts expressing pro-N-cadherin). In some embodiments, the biomarker is pro-N-Cadherin. In some embodiments, the biomarker comprises fibroblast cells expressing pro-N-Cadherin.

In other embodiments, the antibody comprises an antibody against pro-N-cadherin. In certain embodiments, the antibody comprises a monoclonal antibody (mAb).

Suitable pro-N-cadherin antibodies are antibodies that are able to bind specifically to pro-N-cadherin. In other words, they are antibodies that specifically bind to the N-terminal pro-N-cadherin region of N-cadherin that is cleaved to form N-cadherin. Suitable antibodies may bind the polypeptide sequence of the proregion of N-cadherin, (e.g. MCRIAGALRTLLPLLAALLQASVEASGEIALCK-TGFPEDVYSAVLSKDVHEGQPLLNVK FSNCN GKRKVQYESSEPADFKVDEDGMVYAVRSFPLSSE-HAKFLIYAQDKETQEKWQVAVKLS LKPTL TEESVKESAEVEEIVFPRQFSKHSGHLQRQKR (SEQ ID NO:1) taken from sequence of human N-cadherin, (GenBank™ accession NM_001792)). The antibody may bind an epitope of pro-N-cadherin that is linear or bind to a secondary structure formed in the pro-N-cadherin domain. The antibodies contemplated for use in the invention are antibodies specific to the pro-N-cadherin peptide (N-cadherin propeptide) and do not bind to the mature form of N-cadherin. As shown herein, pro-N-cadherin is specifically expressed on pathological fibroblast cells. As such, the use of an antibody specific to pro-N-cadherin allows for the specific targeting and killing of pathological fibroblast cells in contrast to an antibody that binds to the mature form of N-cadherin, which is found on other normal cell types (e.g. heart). Thus, the present invention, in one embodiment, provides a targeted therapy, e.g. antibody therapy against pro-N-cadherin that allows for the specific targeting of pathological fibroblast cells expressing pro-N-cadherin. One skilled in the art would be able to determine suitable antibodies for use in the present invention. Suitable examples include, but are not limited to, pro-N-cadherin antibody described in Wahl et al., (see, e.g., J Biol Chem. 2003; 278(19):17269-17276; Maret D, et al., Neoplasia (New York, N.Y.). 2010; 12(12):1066-1080). Further a pro-N-cadherin antibody is commercially available from R&D systems (human N-cadherin propeptide antibody, available from Bio-Techne Corporation, Minneapolis, Minn.). The antibodies contemplated herein do not bind to the mature form of N-cadherin or non-pathological fibroblast cells.

The antibodies specific to pro-N-cadherin include whole antibodies (e.g., IgG, IgA, IgE, IgM, or IgD), monoclonal antibodies, polyclonal antibodies, and chimeric antibodies, humanized antibodies, and antibody fragments, including single chain variable fragments (ScFv), single domain antibody, and antigen-binding fragments, among others. In a preferred embodiment, the antibody is a monoclonal antibody.

In some embodiments, the anti-cancer drug/therapy is administered before the antibody. In other embodiments, the antibody is administered before the anti-cancer drug/ therapy. In yet other embodiments, the antibody and anti-cancer drug/therapy are administered concurrently.

Pro-N-cadherin antibodies may be provided in combination with liposomes, nanoparticles or other analogous carriers loaded with an anti-cancer drug/therapy. Methods of preparing such compositions are known in the field (see, for example, Sugano et al., Antibody Targeting of Doxorubicin-loaded Liposomes Suppresses the Growth and Metastatic Spread of Established Human Lung Tumor Xenografts in Severe Combined Immunodeficient Mice, *Cancer Research* 60, 6942-6949, Dec. 15, 2000 and Martin et al., Nanomaterials in Analytical Chemistry, *Analytical Chemistry News &Features*, May 1, 1998; pp. 322 A-327 A).

In some embodiments, the subject is a mammal. In other embodiments, the subject is a human.

In other embodiments, the biological sample is selected from the group consisting of tissues, cells, biopsies, blood, lymph, serum, plasma, urine, saliva, mucus, and tears. In certain embodiments, the sample comprises biopsies.

The present disclosure provides a method of determining the risk of, prognosis of, and/or diagnosis of a condition such as fibrosis or any condition associated with pathological fibroblast cells (e.g., fibroblast cells expressing pro-N-cadherin) on at least one sample obtained from a subject. In one embodiment, the subject is any mammal, but is preferably a human. The method comprises detecting and/or measuring the amount of at least one biomarker within the sample, wherein the biomarker is associated with the risk of, prognosis of, and/or diagnosis of the condition.

The present disclosure may involve obtaining more than one sample, such as two samples, such as three samples, four samples or more from subjects, and preferably the same subject. This allows the relative comparison of expression both in the presence or absence of at least biomarker (e.g. one nucleic acid) and/or the level of expression of the at least biomarker (e.g. one nucleic acid) between the two samples. Alternatively, a single sample may be compared against a "standardized" sample, such a sample comprising material or data from several samples, preferably also from several subjects.

Before analyzing the sample, it will often be desirable to perform one or more sample preparation operations upon the sample. Typically, these sample preparation operations will include such manipulations as concentration, suspension, extraction of intracellular material.

Any method required for the processing of a sample prior to detection by any of the methods noted herein falls within the scope of the present disclosure. These methods are typically well known by a person skilled in the art.

It is within the general scope of the present disclosure to provide methods for the detection of protein biomarker. An aspect of the present disclosure relates to the detection of the proteins as described in the plots and graphs of the figures contained herein. The present invention detects the protein of the pro-N-cadherin using a method that specifically detects the protein pro-N-cadherin and does not detect the processed or mature form of N-cadherin (e.g. the processed protein missing the pro-N-cadherin region).

As used herein, the term "detect" or "determine the presence of" refers to the qualitative measurement of undetectable, low, normal, or high concentrations of one or more biomarkers such as, for example, polypeptides of the pro-N-cadherin. Detection may include 1) detection in the sense of presence versus absence of one or more biomarkers as well as 2) the registration/quantification of the level or degree of expression of one or more biomarkers, depending on the method of detection employed. The term "quantify" or "quantification" may be used interchangeable, and refer to a process of determining the quantity or abundance of a substance in a sample (e.g., a biomarker), whether relative or absolute. For example, quantification may be determined by methods including but not limited to, any method able to detect proteins for example, immunohistochemistry, flow cytometry, band intensity on a Western blot, or by various other methods known in the art.

The detection of one or more biomarker molecules allows for the classification, diagnosis and prognosis of a condition such as fibrosis or any condition associated with pathological fibroblast cells (e.g., fibroblast cells expressing pro-N-cadherin). The classification of such conditions is of relevance both medically and scientifically and may provide important information useful for the diagnosis, prognosis and treatment of the condition. The diagnosis of a condition such as fibrosis or any condition associated with pathological fibroblast cells (e.g., fibroblast cells expressing pro-N-cadherin) is the affirmation of the presence of the condition, as is the object of the present disclosure, on the expression of at least one biomarker herein. Prognosis is the estimate or prediction of the probable outcome of a condition such as fibrosis and the prognosis of such is greatly facilitated by increasing the amount of information on the particular condition. The method of detection is thus a central aspect of the present disclosure.

Any method of detection falls within the general scope of the present disclosure. The detection methods may be generic for the detection of polypeptides and the like. The detection methods may be directed towards the scoring of a presence or absence of one or more biomarker molecules or may be useful in the detection of expression levels.

The detection methods can be divided into two categories herein referred to as in situ methods or screening methods. The term in situ method refers to the detection of protein molecules in a sample wherein the structure of the sample has been preserved. This may thus be a biopsy wherein the structure of the tissue is preserved. In situ methods are generally histological i.e. microscopic in nature and include but are not limited to methods such as: immunohistochemistry or any in situ methods able to detect proteins and polypeptides.

Screening methods generally employ techniques of molecular biology and most often require the preparation of the sample material in order to access the polypeptide molecules to be detected. Screening methods include, but are not limited to methods such as: flow cytometry, Western blot analysis, enzyme-linked immunosorbent assay (ELISA), and immunoelectrophoresis. Other methods understood and known by one skilled in the art for detecting proteins is contemplated for use in the present methods.

One aspect of the present disclosure is to provide a probe which can be used for the detection of a polypeptide molecule as defined herein. A probe as defined herein is a specific agent used to detect polypeptides by specifically binding to the protein, e.g. pro-N-cadherin. For example, an antibody or fragment thereof specific to pro-N-cadherin protein can be used as a probe to detect the biomarker, e.g. pro-N-cadherin in a sample. A probe may be labeled, tagged or immobilized or otherwise modified according to the requirements of the detection method chosen. A label or a tag is an entity making it possible to identify a compound to which it is associated. It is within the scope of the present disclosure to employ probes that are labeled or tagged by any means known in the art such as but not limited to: radioactive labeling, fluorescent labeling and enzymatic labeling. Furthermore the probe, labeled or not, may be immobilized to facilitate detection according to the detection method of choice and this may be accomplished according to the preferred method of the particular detection method.

The probes used may be to one or more biomarkers as disclosed herein. In a preferred embodiment, the probe is an antibody to pro-N-cadherin.

Another aspect of the present disclosure regards the detection of a biomarker which is a polypeptide molecules by any method known in the art. In the following are given examples of various detection methods that can be employed for this purpose, and the present disclosure includes all the mentioned methods, but is not limited to any of these.

Immunohistochemistry (IHC) involves the process of selectively imaging proteins in cells of a tissue section by using antibodies binding specifically to protein. Immunohistochemical staining is widely used in the diagnosis of abnormal cells such as those found in pathological cells (e.g., pathological fibroblast cells). Visualizing an antibody-antigen interaction can be accomplished in a number of ways known in the art, including, but not limited to, using an antibody conjugated to an enzyme, such as peroxidase, that can catalyze a color-producing reaction (e.g. immunoperoxidase staining), an antibody tagged or conjugated with a fluorophore, such as fluorescein or rhodamine (e.g. immunofluorescence), among others.

A probe used in IHC (e.g. an antibody or fragment thereof) can be labeled with a radioactive, fluorescent or antigenic tag, so that the probe's location and quantity in the tissue can be determined using autoradiography, fluorescence microscopy or immunoassay, respectively. The sample may be any sample as herein described. The probe is likewise a probe according to any probe based upon the biomarkers mentioned herein.

Flow cytometery can be used in the methods of detecting described herein. Flow cytometry is a laser- or impedance-based method that allows for cell counting, cell sorting, and biomarker detection by suspending cells in a stream of fluid and passing them through an electronic detection apparatus. The present methods include the use of flow cytometry to detect biomarkers on cells within samples taken from the subject. Suitable methods of flow cytometry are known in the art. In one suitable method, an antibody to pro-N-cadherin can be used in conjunction with a fluorescently tagged secondary antibody. In some embodiments, the pro-N-cadherin antibody may be directly conjugated to a fluorescence-tag. Methods of fluorescence-activated cell sorting (FACS) may also be used. It provides a method for sorting a heterogeneous mixture of biological cells into two or more containers, one cell at a time, based upon the specific light scattering and fluorescent characteristics of each cell.

Western blot (sometimes called the protein immunoblot) can be used in the detection methods described herein. Western blot methods are known in the art. For example, a sample may be separated by gel electrophoresis. Following electrophoretic separation, the proteins within the gel are transferred to a membrane (e.g., nitrocellulose or PVDF) on which the protein is then detected using a suitable probe, e.g. antibody specific to the biomarker. Using various methods such as staining, immunofluorescence, and radioactivity, visualization of the protein of interest can be detected on the membrane. Other suitable related techniques that can be used include, but are not limited to, dot blot analysis, and quantitative dot blot.

The enzyme-linked immunosorbent assay (ELISA) can also be used in the methods described herein. In some embodiments, the ELISA includes a solid-phase enzyme immunoassay (EIA) to detect the presence of a protein in a sample. ELISA also uses a probe, e.g. antibody specific to the biomarker to detect the biomarker within the sample. Suitable methods of performing ELISA are known in the art.

Immunoelectrophoresis can also be used in the methods described herein, for example, a number of biochemical methods for separation and characterization of proteins based on electrophoresis and reaction with antibodies are known in the art. The methods usually use antibodies specific to the protein to be detected.

In situ hybridization (ISH) applies and extrapolates the technology of nucleic acid and/or polypeptide hybridization to the single cell level, and, in combination with the art of cytochemistry, immunocytochemistry and immunohistochemistry, permits the maintenance of morphology and the identification of cellular markers to be maintained and identified, allows the localization of sequences to specific cells within populations, such as tissues and blood samples. ISH is a type of hybridization that uses a complementary nucleic acid to localize one or more specific nucleic acid sequences in a portion or section of tissue (in situ), or, if the tissue is small enough, in the entire tissue (whole mount ISH). DNA ISH can be used to determine the structure of chromosomes and the localization of individual genes and optionally their copy numbers. Fluorescent DNA ISH (FISH) can for example be used in medical diagnostics to assess chromosomal integrity. RNA ISH is used to assay expression and gene expression patterns in a tissue/across cells, such as the expression of miRNAs/nucleic acid molecules. Sample cells are treated to increase their permeability to allow the probe to enter the cells, the probe is added to the treated cells, allowed to hybridize at pertinent temperature, and then excess probe is washed away. A complementary probe is labeled with a radioactive, fluorescent or antigenic tag, so that the probe's location and quantity in the tissue can be determined using autoradiography, fluorescence microscopy or immunoassay, respectively. The sample may be any sample as herein described. The probe is likewise a probe according to any probe based upon the biomarkers mentioned herein.

In situ PCR is the PCR based amplification of the target nucleic acid sequences prior to ISH. For detection of RNA, an intracellular reverse transcription (RT) step is introduced to generate complementary DNA from RNA templates prior to in situ PCR. This enables detection of low copy RNA sequences.

Prior to in situ PCR, cells or tissue samples are fixed and permeabilized to preserve morphology and permit access of the PCR reagents to the intracellular sequences to be amplified. PCR amplification of target sequences is next performed either in intact cells held in suspension or directly in cytocentrifuge preparations or tissue sections on glass slides. In the former approach, fixed cells suspended in the PCR reaction mixture are thermally cycled using conventional thermal cyclers. After PCR the cells are cytocentrifugated onto glass slides with visualization of intracellular PCR products by ISH or immunohistochemistry. In situ PCR on glass slides is performed by overlaying the samples with the PCR mixture under a coverslip which is then sealed to prevent evaporation of the reaction mixture. Thermal cycling is achieved by placing the glass slides either directly on top of the heating block of a conventional or specially designed thermal cycler or by using thermal cycling ovens. Detection of intracellular PCR-products is achieved by one of two entirely different techniques. In indirect in situ PCR by ISH with PCR-product specific probes, or in direct in situ PCR without ISH through direct detection of labeled nucleotides (e.g. digoxigenin-11-dUTP, fluorescein-dUTP, $^3$H-CTP or biotin-16-dUTP) which have been incorporated into the PCR products during thermal cycling.

An embodiment of the present disclosure concerns the method of in situ PCR as mentioned herein above for the detection of nucleic acid molecules as detailed herein.

A microarray is a microscopic, ordered array of nucleic acids, proteins, small molecules, cells or other substances that enables parallel analysis of complex biochemical samples. A DNA microarray consists of different nucleic acid probes, known as capture probes that are chemically attached to a solid substrate, which can be a microchip, a glass slide or a microsphere-sized bead. Microarrays can be used e.g. to measure the expression levels of large numbers of polypeptides/proteins/nucleic acids simultaneously.

Microarrays can be fabricated using a variety of technologies, including printing with fine-pointed pins onto glass slides, photolithography using pre-made masks, photolithography using dynamic micromirror devices, ink-jet printing, or electrochemistry on microelectrode arrays.

An aspect of the present disclosure regards the use of microarrays for the expression profiling of biomarkers in conditions such as fibrosis or conditions associated with pathological fibroblast cells. For this purpose, and by way of example, RNA is extracted from a cell or tissue sample, the small RNAs (18-26-nucleotide RNAs) are size-selected from total RNA using denaturing polyacrylamide gel electrophoresis (PAGE). Then oligonucleotide linkers are attached to the 5' and 3' ends of the small RNAs and the resulting ligation products are used as templates for an RT-PCR reaction with 10 cycles of amplification. The sense strand PCR primer has a Cy3 fluorophore attached to its 5' end, thereby fluorescently labelling the sense strand of the PCR product. The PCR product is denatured and then hybridized to the microarray. A PCR product, referred to as the target nucleic acid that is complementary to the corresponding RNA capture probe sequence on the array will hybridize, via base pairing, to the spot at which the capture probes are affixed. The spot will then fluoresce when excited using a microarray laser scanner. The fluorescence intensity of each spot is then evaluated in terms of the number of copies of a particular biomarker, using a number of positive and negative controls and array data normalization methods, which will result in assessment of the level of expression of a particular biomarker.

Several types of microarrays can be employed such as spotted oligonucleotide microarrays, pre-fabricated oligonucleotide microarrays or spotted long oligonucleotide arrays.

In spotted oligonucleotide microarrays the capture probes are oligonucleotides complementary to nucleic acid sequences. This type of array is typically hybridized with amplified.

PCR products of size-selected small RNAs from two samples to be compared that are labelled with two different fluorophores. Alternatively, total RNA containing the small RNA fraction is extracted from the abovementioned two samples and used directly without size-selection of small RNAs, and 3' end labeled using T4 RNA ligase and short RNA linkers labelled with two different fluorophores. The samples can be mixed and hybridized to one single microarray that is then scanned, allowing the visualization of up-regulated and down-regulated biomarker genes in one go. The downside of this is that the absolute levels of gene expression cannot be observed, but the cost of the experiment is reduced by half. Alternatively, a universal reference can be used, comprising of a large set of fluorophore-labelled oligonucleotides, complementary to the array capture probes.

In pre-fabricated oligonucleotide microarrays or single-channel microarrays, the probes are designed to match the sequences of known or predicted biomarkers. There are commercially available designs that cover complete genomes from companies such as Affymetrix, or Agilent. These microarrays give estimations of the absolute value of gene expression and therefore the comparison of two conditions requires the use of two separate microarrays.

Spotted long oligonucleotide arrays are composed of 50 to 70-mer oligonucleotide capture probes, and are produced by either ink-jet or robotic printing. Short Oligonucleotide Arrays are composed of 20-25-mer oligonucleotide probes, and are produced by photolithographic synthesis (Affymetrix) or by robotic printing. More recently, Maskless Array Synthesis from NimbleGen Systems has combined flexibility with large numbers of probes. Arrays can contain up to 390,000 spots, from a custom array design.

The terms "PCR reaction", "PCR amplification", "PCR", "pre-PCR", "Q-PCR", "real-time quantitative PCR" and "real-time quantitative RT-PCR" are interchangeable terms used to signify use of a nucleic acid amplification system, which multiplies the target nucleic acids being detected. Examples of such systems include the polymerase chain reaction (PCR) system and the ligase chain reaction (LCR) system. Other methods recently described and known to the person of skill in the art are the nucleic acid sequence-based amplification and Q Beta Replicase systems. The products formed by said amplification reaction may or may not be monitored in real time or only after the reaction as an end-point measurement.

Real-time quantitative RT-PCR is a modification of polymerase chain reaction used to rapidly measure the quantity of a product of polymerase chain reaction. It is preferably done in real-time, thus it is an indirect method for quantitatively measuring starting amounts of DNA, complementary DNA or ribonucleic acid (RNA). This is commonly used for the purpose of determining whether a genetic sequence is present or not, and if it is present the number of copies in the sample. There are 3 methods which vary in difficulty and detail. Like other forms of polymerase chain reaction, the process is used to amplify DNA samples, using thermal cycling and a thermostable DNA polymerase.

The three commonly used methods of quantitative polymerase chain reaction are through agarose gel electrophoresis, the use of SYBR Green, a double stranded DNA dye, and the fluorescent reporter probe. The latter two of these three can be analyzed in real-time, constituting real-time polymerase chain reaction method.

Agarose gel electrophoresis is the simplest method, but also often slow and less accurate then other methods, depending on the running of an agarose gel via electrophoresis. It cannot give results in real time. The unknown sample and a known sample are prepared with a known concentration of a similarly sized section of target DNA for amplification. Both reactions are run for the same length of time in identical conditions (preferably using the same primers, or at least primers of similar annealing temperatures). Agarose gel electrophoresis is used to separate the products of the reaction from their original DNA and spare primers. The relative quantities of the known and unknown samples are measured to determine the quantity of the unknown. This method is generally used as a simple measure of whether the probe target sequences are present or not, and rarely as 'true' Q-PCR.

Using SYBR Green dye is more accurate than the gel method, and gives results in real time. A DNA binding dye binds all newly synthesized double stranded (ds)DNA and an increase in fluorescence intensity is measured, thus allowing initial concentrations to be determined. However, SYBR Green will label all dsDNA including any unexpected PCR products as well as primer dimers, leading to potential complications and artefacts. The reaction is prepared as usual, with the addition of fluorescent dsDNA dye. The reaction is run, and the levels of fluorescence are monitored; the dye only fluoresces when bound to the dsDNA. With reference to a standard sample or a standard curve, the dsDNA concentration in the PCR can be determined.

The fluorescent reporter probe method is the most accurate and most reliable of the methods. It uses a sequence-specific nucleic acid-based probe so as to only quantify the probe sequence and not all double stranded DNA. It is commonly carried out with DNA based probes with a fluorescent reporter and a quencher held in adjacent positions, so-called dual-labelled probes. The close proximity of the reporter to the quencher prevents its fluorescence; it is only on the breakdown of the probe that the fluorescence is detected. This process depends on the 5' to 3' exonuclease activity of the polymerase involved. The real-time quantitative PCR reaction is prepared with the addition of the dual-labelled probe. On denaturation of the double-stranded DNA template, the probe is able to bind to its complementary sequence in the region of interest of the template DNA (as the primers will too). When the PCR reaction mixture is heated to activate the polymerase, the polymerase starts synthesizing the complementary strand to the primed single stranded template DNA. As the polymerization continues it reaches the probe bound to its complementary sequence, which is then hydrolyzed due to the 5'-3' exonuclease activity of the polymerase thereby separating the fluorescent reporter and the quencher molecules. This results in an increase in fluorescence, which is detected. During thermal cycling of the real-time PCR reaction, the increase in fluorescence, as released from the hydrolyzed dual-labelled probe in each PCR cycle is monitored, which allows accurate determination of the final, and so initial, quantities of DNA.

Any method of PCR that can determine the expression of a nucleic acid molecule as defined herein falls within the scope of the present disclosure. A preferred embodiment of the present disclosure includes the real-time quantitative RT-PCR method, based on the use of either SYBR Green dye or a dual-labelled probe for the detection and quantification of nucleic acids according to the herein described.

Yet another aspect of the present disclosure provides a method of treating and/or preventing fibrosis in a subject, the method comprising, consisting of, or consisting essentially of administering to the subject a therapeutically effective amount of a Pro-N-Cadherin inhibiting molecule such that the fibrosis is treated in the subject.

The targeting of Pro-N-Cadherin offers multiple routes for inhibiting its expression and/or function. Such inhibitory molecules may prevent the expression of Pro-N-Cadherin and/or inhibit the function of Pro-N-Cadherin and/or induce the cleaving of Pro-N-Cadherin to its mature form, N-Cadherin. Suitable inhibitory molecules include, but are not limited to, small molecules, antibodies, miRNAs, antisense RNAs, oligonucleotides, aptamers, siRNAs, peptides, polypeptides, and combinations thereof.

In this specification "antibody" includes a fragment or derivative of an antibody, or a synthetic antibody or synthetic antibody fragment.

Antibodies may be provided in isolated or purified form. Antibodies may be formulated as a pharmaceutical composition or medicament.

Suitable anti-Pro-N-Cadherin antibodies will preferably bind to Pro-N-Cadherin (the antigen), preferably human Pro-N-Cadherin, and may have a dissociation constant ($K_D$) of one of 1 µM, 100 µM, 10 µM, 1 nM or 100 pM. Binding affinity of an antibody for its target is often described in terms of its dissociation constant ($K_D$). Binding affinity can be measured by methods known in the art, such as by Surface Plasmon Resonance (SPR), or by a radiolabeled antigen binding assay (RIA) performed with the Fab version of the antibody and antigen molecule.

Anti-Pro-N-Cadherin antibodies may be antagonist antibodies that inhibit or reduce a biological activity of Pro-N-Cadherin. Anti-Pro-N-Cadherin antibodies may be antagonist antibodies that inhibit or reduce any function of Pro-N-Cadherin, in particular signaling.

Anti-Pro-N-Cadherin antibodies may be neutralizing antibodies that neutralize the biological effect of Pro-N-Cadherin, e.g. its ability to initiate productive signaling mediated by binding of Pro-N-Cadherin.

In some embodiments, the antibody is a polyclonal antibody. In other embodiments, the antibody is a monoclonal. An example of a known anti-Pro-N-Cadherin monoclonal antibody comprises 10A10. In certain embodiments, monoclonal antibody is a humanized monoclonal antibody.

In view of today's techniques in relation to monoclonal antibody technology, antibodies can be prepared to most antigens. The antigen-binding portion may be a part of an antibody (for example a Fab fragment) or a synthetic antibody fragment (for example a single chain Fv fragment [ScFv]). Suitable monoclonal antibodies to selected antigens may be prepared by known techniques, for example those disclosed in "Monoclonal Antibodies: A manual of techniques", H Zola (CRC Press, 1988) and in "Monoclonal Hybridoma Antibodies: Techniques and Applications", J G R Hurrell (CRC Press, 1982). Chimaeric antibodies are discussed by Neuberger et al (1988, 8th International Biotechnology Symposium Part 2, 792-799).

Monoclonal antibodies (mAbs) are useful in the methods of the disclosure and are a homogenous population of antibodies specifically targeting a single epitope on an antigen.

Polyclonal antibodies are useful in the methods of the disclosure. Monospecific polyclonal antibodies are preferred. Suitable polyclonal antibodies can be prepared using methods well known in the art.

Antigen binding fragments of antibodies, such as Fab and Fab$_2$ fragments may also be used/provided as can genetically engineered antibodies and antibody fragments. The variable heavy ($V_H$) and variable light ($V_L$) domains of the antibody are involved in antigen recognition, a fact first recognized by early protease digestion experiments. Further confirmation was found by "humanization" of rodent antibodies. Variable domains of rodent origin may be fused to constant domains of human origin such that the resultant antibody retains the antigenic specificity of the rodent parented antibody (see, e.g., Morrison et al (1984) Proc. Natl. Acad. Sd. USA 81, 6851-6855).

That antigenic specificity is conferred by variable domains and is independent of the constant domains is known from experiments involving the bacterial expression of antibody fragments, all containing one or more variable domains. These molecules include Fab-like molecules (see, e.g., Better et al (1988) Science 240, 1041); Fv molecules (see, e.g., Skerra et al (1988) Science 240, 1038); single-chain Fv (ScFv) molecules where the $V_H$ and $V_L$ partner domains are linked via a flexible oligopeptide (see, e.g., Bird et al (1988) Science 242, 423; Huston et al (1988) Proc. Natl. Acad. Sd. USA 85, 5879) and single domain antibodies (dAbs) comprising isolated V domains (see, e.g., Ward et al (1989) Nature 341, 544). A general review of the techniques involved in the synthesis of antibody fragments which retain their specific binding sites is to be found in Winter & Milstein (1991) Nature 349, 293-299.

By "ScFv molecules" we mean molecules wherein the $V_H$ and $V_L$ partner domains are covalently linked, e.g. by a flexible oligopeptide.

Fab, Fv, ScFv and dAb antibody fragments can all be expressed in and secreted from *E. coli*, thus allowing the facile production of large amounts of the said fragments.

Whole antibodies, and $F(ab')_2$ fragments are "bivalent". By "bivalent" we mean that the said antibodies and $F(ab')_2$ fragments have two antigen combining sites. In contrast, Fab, Fv, ScFv and dAb fragments are monovalent, having only one antigen combining site. Synthetic antibodies which bind to Pro-N-Cadherin may also be made using phage display technology as is well known in the art.

Antibodies may be produced by a process of affinity maturation in which a modified antibody is generated that has an improvement in the affinity of the antibody for antigen, compared to an unmodified parent antibody. Affinity-matured antibodies may be produced by procedures known in the art, e.g., Marks et al., Rio/Technology 10:779-783 (1992); Barbas et al. Proc Nat. Acad. Sci. USA 91:3809-3813 (1994); Schier et al. Gene 169:147-155 (1995); Yelton et al. J. Immunol. 155:1994-2004 (1995); Jackson et al., J. Immunol. 154(7):331 0-15 9 (1995); and Hawkins et al, J. Mol. Biol. 226:889-896 (1992).

Antibodies according to the present disclosure preferably exhibit specific binding to Pro-N-Cadherin. An antibody that specifically binds to a target molecule preferably binds the target with greater affinity, and/or with greater duration than it binds to other targets. In one embodiment, the extent of binding of an antibody to an unrelated target is less than about 10% of the binding of the antibody to the target as measured, e.g., by ELISA, or by a radioimmunoassay (RIA). Alternatively, the binding specificity may be reflected in terms of binding affinity where the antibody binds to Pro-N-Cadherin with a $K_D$ that is at least 0.1 order of magnitude (i.e. 0.1×10n, where n is an integer representing the order of magnitude) greater than the $K_D$ of the antibody towards another target molecule.

Antibodies may be detectably labelled or, at least, capable of detection. Such antibodies being useful for both in vivo (e.g. imaging methods) and in vitro (e.g. assay methods) applications. For example, the antibody may be labelled with a radioactive atom or a colored molecule or a fluorescent molecule or a molecule which can be readily detected in any other way. Suitable detectable molecules include fluorescent proteins, luciferase, enzyme substrates, and radiolabels. The binding moiety may be directly labelled with a detectable label or it may be indirectly labelled. For example, the binding moiety may be an unlabeled antibody which can be detected by another antibody which is itself labelled. Alternatively, the second antibody may have bound to it biotin and binding of labelled streptavidin to the biotin is used to indirectly label the first antibody.

Aspects of the present disclosure include bi-specific antibodies, e.g. composed of two different fragments of two different antibodies, such that the bi-specific antibody binds two types of antigen. One of the antigens is Pro-N-Cadherin, the bi-specific antibody comprising a fragment as described herein that binds to Pro-N-Cadherin. The antibody may contain a different fragment having affinity for a second antigen, which may be any desired antigen. Techniques for the preparation of bi-specific antibodies are well known in the art, e.g. see Mueller, D et al., (2010 Biodrugs 24 (2): 89-98), Wozniak-Knopp G et al., (2010 Protein Eng Des 23 (4): 289-297. Baeuerle, P A et al., (2009 Cancer Res 69 (12): 4941-4944).

In some embodiments, the bispecific antibody is provided as a fusion protein of two single-chain variable fragments (scFV) format, comprising a $V_H$ and $V_L$ of a Pro-N-Cadherin binding antibody or antibody fragment, and a $V_H$ and $V_L$ of an another antibody or antibody fragment.

Bispecific antibodies and bispecific antigen binding fragments may be provided in any suitable format, such as those formats described in Kontermann MAbs 2012, 4(2): 182-197, which is hereby incorporated by reference in its entirety.

Methods for producing bispecific antibodies include chemically crosslinking antibodies or antibody fragments, e.g. with reducible disulfide or non-reducible thioether bonds, for example as described in Segal and Bast, 2001. Production of Bispecific Antibodies. Current Protocols in Immunology. 14:IV:2.13:2.13.1-2.13.16, which is hereby incorporated by reference in its entirety. For example, N-succinimidyl-3-(−2-pyridyldithio)-propionate (SPDP) can be used to chemically crosslink e.g. Fab fragments via hinge region SH— groups, to create disulfide-linked bispecific $F(ab)_2$ heterodimers.

Other methods for producing bispecific antibodies include fusing antibody-producing hybridomas e.g. with polyethylene glycol, to produce a quadroma cell capable of secreting bispecific antibody, for example as described in D. M. and Bast, B. J. 2001. Production of Bispecific Antibodies. Current Protocols in Immunology. 14:IV:2.13:2.13.1-2.13.16.

Bispecific antibodies and bispecific antigen binding fragments can also be produced recombinantly, by expression from e.g. a nucleic acid construct encoding polypeptides for the antigen binding molecules, for example as described in Antibody Engineering: Methods and Protocols, Second Edition (Humana Press, 2012), at Chapter 40: Production of Bispecific Antibodies: Diabodies and Tandem scFv (Hornig and Farber-Schwarz), or French, How to make bispecific antibodies, Methods Mol. Med. 2000; 40:333-339.

For example, a DNA construct encoding the light and heavy chain variable domains for the two antigen binding domains (i.e. the light and heavy chain variable domains for the antigen binding domain capable of binding Pro-N-Cadherin, and the light and heavy chain variable domains for the antigen binding domain capable of binding to another target protein), and including sequences encoding a suitable linker or dimerization domain between the antigen binding domains can be prepared by molecular cloning techniques. Recombinant bispecific antibody can thereafter be produced by expression (e.g. in vitro) of the construct in a suitable host cell (e.g. a mammalian host cell), and expressed recombinant bispecific antibody can then optionally be purified.

Peptide or polypeptide based Pro-N-Cadherin binding agents may be based on the Pro-N-Cadherin protein or a fragment of Pro-N-Cadherin.

In other embodiments a Pro-N-Cadherin inhibiting molecule may be provided in the form of a small molecule inhibitor of Pro-N-Cadherin.

Peptide or polypeptide based Pro-N-Cadherin inhibitory molecules may be based on Pro-N-Cadherin, e.g. mutant, variant or binding fragment of Pro-N-Cadherin. Suitable peptide or polypeptide-based molecules may bind to Pro- N-Cadherin in a manner that does not lead to initiation of signal transduction or produces sub-optimal signaling.

In some embodiments a pro-N-Cadherin inhibitory molecule may be provided in the form of a small molecule inhibitor of pro-N-Cadherin.

The inventors have identified that pro-N-Cadherin expression is consistent with the molecular mechanism of fibrosis and that inhibition of Pro-N-Cadherin activity and/or induce the cleavage of Pro-N-Cadherin to its mature form N-cadherin leads to a reduction in the molecular basis for fibrosis. Accordingly, in some aspects of the present disclosure treatment, prevention or alleviation of fibrosis may be provided by administration of an inhibitory molecule capable of preventing or reducing the expression of Pro-N-Cadherin by cells of the subject, e.g. by fibroblasts or myofibroblasts.

In some embodiments an inhibitory molecule capable of preventing or reducing the expression of Pro-N-Cadherin may be an oligonucleotide capable of repressing or silencing expression of Pro-N-Cadherin.

Accordingly, the present disclosure also includes the use of techniques known in the art for the therapeutic down regulation of Pro-N-Cadherin expression. These include the use of antisense oligonucleotides and RNA interference (RNAi). As in other aspects of the present disclosure, these techniques may be used in the treatment of fibrosis.

Accordingly, in one aspect of the present disclosure a method of treating or preventing fibrosis is provided, the method comprising, consisting of, or consisting essentially of administering to a subject in need of treatment a therapeutically effective amount of Pro-N-Cadherin inhibiting molecule capable of preventing or reducing the expression of Pro-N-Cadherin, wherein the molecule comprises a vector comprising a therapeutic oligonucleotide capable of repressing or silencing expression of Pro-N-Cadherin.

In another aspect of the present invention a method of treating or preventing fibrosis is provided, the method comprising, consisting of, or consisting essentially of administering to a subject in need of treatment a therapeutically effective amount of an agent capable of preventing or reducing the expression of Pro-N-Cadherin, wherein the agent comprises an oligonucleotide vector, optionally a viral vector, encoding a therapeutic oligonucleotide capable of being expressed in cells of the subject, the expressed therapeutic oligonucleotide being capable of repressing or silencing expression of Pro-N-Cadherin.

The ability of an inhibiting molecule to prevent or reduce the expression of Pro-N-Cadherin may be assayed by determining the ability of the agent to inhibit Pro-N-Cadherin gene or protein expression by fibroblasts or myofibroblasts, e.g. cardiac/atrial fibroblasts or myofibroblasts.

Reducing the amount of Pro-N-Cadherin available for expression and/or cleavage to the mature form, N-Cadherin, provides an alternative means of reducing the level of Pro-N-Cadherin stimulated signaling. Accordingly, in related aspects of the present disclosure, treatment, prevention or alleviation of fibrosis may be provided by administration of an inhibitory molecule capable of preventing or reducing the expression of Pro-N-Cadherin by cells of the subject, e.g. by fibroblasts or myofibroblasts.

In some embodiments an inhibiting molecule capable of preventing or reducing the expression of Pro-N-Cadherin may be an oligonucleotide capable of repressing or silencing expression of Pro-N-Cadherin.

Accordingly, the present disclosure also includes the use of techniques known in the art for the therapeutic down regulation of Pro-N-Cadherin expression. These include the use of antisense oligonucleotides and RNA interference (RNAi). As in other aspects of the present disclosure, these techniques may be used in the treatment of fibrosis.

Accordingly, one aspect of the present disclosure provides a method of treating or preventing fibrosis, the method comprising, consisting of, or consisting essentially of administering to a subject in need of treatment a therapeutically effective amount of an inhibiting molecule capable of preventing or reducing the expression of Pro-N-Cadherin, wherein the inhibiting molecule comprises a vector comprising a therapeutic oligonucleotide capable of repressing or silencing expression of Pro-N-Cadherin.

In another aspect of the present disclosure a method of treating or preventing fibrosis is provided, the method comprising, consisting of, or consisting essentially of administering to a subject in need of treatment a therapeutically effective amount of an inhibiting molecule capable of preventing or reducing the expression of Pro-N-Cadherin, wherein the inhibiting molecule comprises an oligonucleotide vector, optionally a viral vector, encoding a therapeutic oligonucleotide capable of being expressed in cells of the subject, the expressed therapeutic oligonucleotide being capable of repressing or silencing expression of Pro-N-Cadherin.

The ability of an inhibiting molecule to prevent or reduce the expression of Pro-N-Cadherin may be assayed by determining the ability of the agent to inhibit Pro-N-Cadherin gene or protein expression by fibroblasts or myofibroblasts, e.g. cardiac/atrial fibroblasts or myofibroblasts.

Aptamers, also called nucleic acid ligands, are nucleic acid molecules characterized by the ability to bind to a target molecule with high specificity and high affinity. Almost every aptamer identified to date is a non-naturally occurring molecule.

Aptamers to a given target (e.g. Pro-N-Cadherin) may be identified and/or produced by the method of Systematic Evolution of Ligands by EXponential enrichment (SELEX™). Aptamers and SELEX are described in Tuerk and Gold (Systematic evolution of ligands by exponential enrichment: RNA ligands to bacteriophage T4 DNA polymerase. Science. 1990 Aug. 3; 249(4968):505-10) and in WO91/19813.

Aptamers may be DNA or RNA molecules and may be single stranded or double stranded. The aptamer may comprise chemically modified nucleic acids, for example in which the sugar and/or phosphate and/or base is chemically modified. Such modifications may improve the stability of the aptamer or make the aptamer more resistant to degradation and may include modification at the 2' position of ribose.

Aptamers may be synthesized by methods which are well known to the skilled person. For example, aptamers may be chemically synthesized, e.g. on a solid support.

Solid phase synthesis may use phosphoramidite chemistry. Briefly, a solid supported nucleotide is detritylated, then coupled with a suitably activated nucleoside phosphoramidite to form a phosphite triester linkage. Capping may then occur, followed by oxidation of the phosphite triester with an oxidant, typically iodine. The cycle may then be repeated to assemble the aptamer.

Aptamers can be thought of as the nucleic acid equivalent of monoclonal antibodies and often have $K_D$'s in the nM or pM range, e.g. less than one of 500 nM, 100 nM, 50 nM, 10 nM, 1 nM, 500 pM, 100 pM. As with monoclonal antibodies, they may be useful in virtually any situation in which target binding is required, including use in therapeutic and diagnostic applications, in vitro or in vivo. In vitro diagnostic applications may include use in detecting the presence or absence of a target molecule.

Aptamers according to the present disclosure may be provided in purified or isolated form. Aptamers according to the present disclosure may be formulated as a pharmaceutical composition or medicament.

Suitable aptamers may optionally have a minimum length of one of 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 nucleotides.

Suitable aptamers may optionally have a maximum length of one of 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, or 80 nucleotides.

Suitable aptamers may optionally have a length of one of 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, or 80 nucleotides.

Oligonucleotide molecules, particularly RNA, may be employed to regulate gene expression. These include antisense oligonucleotides, targeted degradation of mRNAs by small interfering RNAs (siRNAs), small molecules, post transcriptional gene silencing (PTGs), developmentally regulated sequence-specific translational repression of mRNA by micro-RNAs (miRNAs) and targeted transcriptional gene silencing.

An antisense oligonucleotide is an oligonucleotide, preferably single stranded, that targets and binds, by complementary sequence binding, to a target oligonucleotide, e.g. mRNA. Where the target oligonucleotide is an mRNA, binding of the antisense to the mRNA blocks translation of the mRNA and expression of the gene product. Antisense oligonucleotides may be designed to bind sense genomic nucleic acid and inhibit transcription of a target nucleotide sequence.

In view of the known nucleic acid sequences for Pro-N-Cadherin, oligonucleotides may be designed to repress or silence the expression of Pro-N-Cadherin. Such oligonucleotides may have any length, but may preferably be short, e.g. less than 100 nucleotides, e.g. 10-40 nucleotides, or 20-50 nucleotides, and may comprise a nucleotide sequence having complete- or near-complementarity (e.g. 80%, 85%, 90%, 91%, 92%, 93%, 94%, 95%, 96%, 97%, 98%, 99% or 100% complementarity) to a sequence of nucleotides of corresponding length in the target oligonucleotide, e.g. the Pro-N-Cadherin mRNA. The complementary region of the nucleotide sequence may have any length, but is preferably at least 5, and optionally no more than 50, nucleotides long, e.g. one of 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 nucleotides.

Repression of Pro-N-Cadherin expression will preferably result in a decrease in the quantity of Pro-N-Cadherin expressed by a cell, e.g. by a fibroblast or myofibroblast. For example, in a given cell the repression of Pro-N-Cadherin by administration of a suitable nucleic acid will result in a decrease in the quantity of Pro-N-Cadherin expressed by that cell relative to an untreated cell. Repression may be partial. Preferred degrees of repression are at least 50%, more preferably one of at least 60%, 70%, 80%, 85% or 90%. A level of repression between 90% and 100% is considered a 'silencing' of expression or function.

A role for the RNAi machinery and small RNAs in targeting of heterochromatin complexes and epigenetic gene silencing at specific chromosomal loci has been demonstrated. Double-stranded RNA (dsRNA)-dependent post transcriptional silencing, also known as RNA interference (RNAi), is a phenomenon in which dsRNA complexes can target specific genes of homology for silencing in a short period of time. It acts as a signal to promote degradation of mRNA with sequence identity. A 20-nt siRNA is generally long enough to induce gene-specific silencing, but short enough to evade host response. The decrease in expression of targeted gene products can be extensive with 90% silencing induced by a few molecules of siRNA. RNAi based therapeutics have been progressed into Phase I, II and III clinical trials for a number of indications (Nature 2009 Jan. 22; 457(7228):426-433).

In the art, these RNA sequences are termed "short or small interfering RNAs" (siRNAs) or "microRNAs" (miRNAs) depending on their origin. Both types of sequence may be used to down-regulate gene expression by binding to complementary RNAs and either triggering mRNA elimination (RNAi) or arresting mRNA translation into protein. siRNAs are derived by processing of long double stranded RNAs and when found in nature are typically of exogenous origin. Micro-interfering RNAs (miRNA) are endogenously encoded small non-coding RNAs, derived by processing of short hairpins. Both siRNA and miRNA can inhibit the translation of mRNAs bearing partially complimentary target sequences without RNA cleavage and degrade mRNAs bearing fully complementary sequences.

Accordingly, the present disclosure provides the use of oligonucleotide sequences for down-regulating the expression of Pro-N-Cadherin.

siRNA ligands are typically double stranded and, in order to optimize the effectiveness of RNA mediated down-regulation of the function of a target gene, it is preferred that the length of the siRNA molecule is chosen to ensure correct recognition of the siRNA by the RISC complex that mediates the recognition by the siRNA of the mRNA target and so that the siRNA is short enough to reduce a host response.

miRNA ligands are typically single stranded and have regions that are partially complementary enabling the ligands to form a hairpin. miRNAs are RNA genes which are transcribed from DNA, but are not translated into protein. A DNA sequence that codes for a miRNA gene is longer than the miRNA. This DNA sequence includes the miRNA sequence and an approximate reverse complement. When this DNA sequence is transcribed into a single-stranded RNA molecule, the miRNA sequence and its reverse-complement base pair to form a partially double stranded RNA segment. The design of microRNA sequences is discussed in John et al, PLoS Biology, 11(2), 1862-1879, 2004.

Typically, the RNA ligands intended to mimic the effects of siRNA or miRNA have between 10 and 40 ribonucleotides (or synthetic analogues thereof), more preferably between 17 and 30 ribonucleotides, more preferably between 19 and 25 ribonucleotides and most preferably between 21 and 23 ribonucleotides. In some embodiments of the invention employing double-stranded siRNA, the molecule may have symmetric 3' overhangs, e.g. of one or two (ribo)nucleotides, typically a UU of dTdT 3' overhang. Based on the disclosure provided herein, the skilled person can readily design suitable siRNA and miRNA sequences, for example using resources such the Ambion siRNA finder. siRNA and miRNA sequences can be synthetically produced and added exogenously to cause gene downregulation or produced using expression systems (e.g. vectors). In a preferred embodiment the siRNA is synthesized synthetically.

Longer double stranded RNAs may be processed in the cell to produce siRNAs (see for example Myers (2003) Nature Biotechnology 21:324-328). The longer dsRNA molecule may have symmetric 3' or 5' overhangs, e.g. of one or two (ribo)nucleotides, or may have blunt ends. The longer dsRNA molecules may be 25 nucleotides or longer. Preferably, the longer dsRNA molecules are between 25 and 30 nucleotides long. More preferably, the longer dsRNA molecules are between 25 and 27 nucleotides long. Most preferably, the longer dsRNA molecules are 27 nucleotides in length. dsRNAs 30 nucleotides or more in length may be expressed using the vector pDECAP (Shinagawa et al., Genes and Dev., 17, 1340-5, 2003).

Another alternative is the expression of a short hairpin RNA molecule (shRNA) in the cell. shRNAs are more stable than synthetic siRNAs. A shRNA consists of short inverted repeats separated by a small loop sequence. One inverted repeat is complimentary to the gene target. In the cell the shRNA is processed by DICER into a siRNA which degrades the target gene mRNA and suppresses expression. In a preferred embodiment the shRNA is produced endogenously (within a cell) by transcription from a vector. shRNAs may be produced within a cell by transfecting the cell with a vector encoding the shRNA sequence under control of a RNA polymerase III promoter such as the human H1 or 7SK promoter or a RNA polymerase II promoter. Alternatively, the shRNA may be synthesised exogenously (in vitro) by transcription from a vector. The shRNA may then be introduced directly into the cell. Preferably, the shRNA molecule comprises a partial sequence of Pro-N-Cadherin. Preferably, the shRNA sequence is between 40 and 100 bases in length, more preferably between 40 and 70 bases in length. The stem of the hairpin is preferably between 19 and 30 base pairs in length. The stem may contain G-U pairings to stabilize the hairpin structure.

siRNA molecules, longer dsRNA molecules or miRNA molecules may be made recombinantly by transcription of a nucleic acid sequence, preferably contained within a vector.

Preferably, the siRNA molecule, longer dsRNA molecule or miRNA molecule comprises a partial sequence of Pro-N-Cadherin.

In one embodiment, the siRNA, longer dsRNA or miRNA is produced endogenously (within a cell) by transcription from a vector. The vector may be introduced into the cell in any of the ways known in the art. Optionally, expression of the RNA sequence can be regulated using a tissue specific (e.g. heart, liver, kidney or eye specific) promoter. In a further embodiment, the siRNA, longer dsRNA or miRNA is produced exogenously (in vitro) by transcription from a vector.

Suitable vectors may be oligonucleotide vectors configured to express the oligonucleotide agent capable of Pro-N-Cadherin repression. Such vectors may be viral vectors or plasmid vectors. The therapeutic oligonucleotide may be incorporated in the genome of a viral vector and be operably linked to a regulatory sequence, e.g. promoter, which drives its expression. The term "operably linked" may include the situation where a selected nucleotide sequence and regulatory nucleotide sequence are covalently linked in such a way as to place the expression of a nucleotide sequence under the influence or control of the regulatory sequence. Thus a regulatory sequence is operably linked to a selected nucleotide sequence if the regulatory sequence is capable of effecting transcription of a nucleotide sequence which forms part or all of the selected nucleotide sequence.

Viral vectors encoding promoter-expressed siRNA sequences are known in the art and have the benefit of long term expression of the therapeutic oligonucleotide. Examples include lentiviral (Nature 2009 Jan. 22; 457 (7228):426-433), adenovirus (Shen et al., FEBS Lett 2003 Mar. 27; 539(1-3)111-4) and retroviruses (Barton and Medzhitov PNAS Nov. 12, 2002 vol. 99, no. 23 14943-14945).

In other embodiments a vector may be configured to assist delivery of the therapeutic oligonucleotide to the site at which repression of Pro-N-Cadherin expression is required. Such vectors typically involve complexing the oligonucleotide with a positively charged vector (e.g., cationic cell penetrating peptides, cationic polymers and dendrimers, and cationic lipids); conjugating the oligonucleotide with small molecules (e.g., cholesterol, bile acids, and lipids), polymers, antibodies, and RNAs; or encapsulating the oligonucleotide in nanoparticulate formulations (Wang et al., AAPS J. 2010 December; 12(4): 492-503).

In one embodiment, a vector may comprise a nucleic acid sequence in both the sense and antisense orientation, such that when expressed as RNA the sense and antisense sections will associate to form a double stranded RNA.

Alternatively, siRNA molecules may be synthesized using standard solid or solution phase synthesis techniques which are known in the art. Linkages between nucleotides may be phosphodiester bonds or alternatives, for example, linking groups of the formula P(O)S, (thioate); P(S)S, (dithioate); P(O)NR'2; P(O)R'; P(O)OR6; CO; or CONR'2 wherein R is H (or a salt) or alkyl (1-12C) and R6 is alkyl (1-9C) is joined to adjacent nucleotides through —O— or —S—.

Modified nucleotide bases can be used in addition to the naturally occurring bases, and may confer advantageous properties on siRNA molecules containing them.

For example, modified bases may increase the stability of the siRNA molecule, thereby reducing the amount required for silencing. The provision of modified bases may also provide siRNA molecules which are more, or less, stable than unmodified siRNA.

The term 'modified nucleotide base' encompasses nucleotides with a covalently modified base and/or sugar. For example, modified nucleotides include nucleotides having sugars which are covalently attached to low molecular weight organic groups other than a hydroxyl group at the 3' position and other than a phosphate group at the 5' position. Thus modified nucleotides may also include 2' substituted sugars such as 2'-O-methyl-; 2'-O-alkyl; 2'-O-allyl; 2'-S-alkyl; 2'-S-allyl; 2'-fluoro-; 2'-halo or azido-ribose, carbocyclic sugar analogues, a-anomeric sugars; epimeric sugars such as arabinose, xyloses or lyxoses, pyranose sugars, furanose sugars, and sedoheptulose.

Modified nucleotides are known in the art and include alkylated purines and pyrimidines, acylated purines and pyrimidines, and other heterocycles. These classes of pyrimidines and purines are known in the art and include pseudoisocytosine, N4,N4-ethanocytosine, 8-hydroxy-N6-methyladenine, 4-acetylcytosine, 5-(carboxyhydroxylmethyl) uracil, 5 fluorouracil, 5-bromouracil, 5-carboxymethylaminomethyl-2-thiouracil, 5-carboxymethylaminomethyl uracil, dihydrouracil, inosine, N6-isopentyl-adenine, 1-methyladenine, 1-methylpseudouracil, 1-methylguanine, 2,2-dimethylguanine, 2-methyladenine, 2-methylguanine, 3-methylcytosine, 5-methylcytosine, N6-methyladenine, 7-methylguanine, 5-methylaminomethyl uracil, 5-methoxy amino methyl-2-thiouracil, -D-mannosylqueosine, 5-methoxycarbonylmethyluracil, 5methoxyuracil, 2 methylthio-N6-isopentenyladenine, uracil-5-oxyacetic acid methyl ester, psueouracil, 2-thiocytosine, 5-methyl-2 thiouracil, 2-thiouracil, 4-thiouracil, 5methyluracil, N-uracil-5-oxyacetic acid methylester, uracil 5-oxyacetic acid, queosine, 2-thiocytosine, 5-propyluracil, 5-propylcytosine, 5-ethyluracil, 5ethylcytosine, 5-butyluracil, 5-pentyluracil, 5-pentylcytosine, and 2,6,diaminopurine, methylpsuedouracil, 1-methylguanine, 1-methylcytosine.

Methods relating to the use of RNAi to silence genes in *C. elegans, Drosophila*, plants, and mammals are known in the art (Fire A, et al., 1998 Nature 391:806-811; Fire, A. Trends Genet. 15, 358-363 (1999); Sharp, P. A. RNA interference 2001. Genes Dev. 15, 485-490 (2001); Hammond, S. M., et al., Nature Rev. Genet. 2, 110-1119 (2001); Tuschl, T. Chem. Biochem. 2, 239-245 (2001); Hamilton, A. et al., Science 286, 950-952 (1999); Hammond, S. M., et al., Nature 404, 293-296 (2000); Zamore, P. D., et al., Cell 101, 25-33 (2000); Bernstein, E., et al., Nature 409, 363-366 (2001); Elbashir, S. M., et al., Genes Dev. 15, 188-200 (2001); WO0129058; WO9932619, and Elbashir S M, et al., 2001 Nature 411:494-498).

Accordingly, the present disclosure provides a nucleic acid that is capable, when suitably introduced into or expressed within a mammalian, e.g. human, cell that otherwise expresses Pro-N-Cadherin, of suppressing Pro-N-Cadherin expression by RNAi.

The nucleic acid may have substantial sequence identity to a portion of Pro-N-Cadherin mRNA, or the complementary sequence to said mRNA.

The nucleic acid may be a double-stranded siRNA. (As the skilled person will appreciate, and as explained further below, a siRNA molecule may include a short 3' DNA sequence also.)

Alternatively, the nucleic acid may be a DNA (usually double-stranded DNA) which, when transcribed in a mammalian cell, yields an RNA having two complementary portions joined via a spacer, such that the RNA takes the form of a hairpin when the complementary portions hybridize with each other. In a mammalian cell, the hairpin structure may be cleaved from the molecule by the enzyme DICER, to yield two distinct, but hybridized, RNA molecules.

Only single-stranded (i.e. non self-hybridized) regions of an mRNA transcript are expected to be suitable targets for RNAi. It is therefore proposed that other sequences very close in the Pro-N-Cadherin mRNA transcript may also be suitable targets for RNAi.

Accordingly, the present disclosure provides nucleic acids that are capable, when suitably introduced into or expressed within a mammalian cell that otherwise expresses Pro-N-Cadherin, of suppressing Pro-N-Cadherin expression by RNAi, wherein the nucleic acid is generally targeted to the sequence of, or portion thereof, of Pro-N-Cadherin.

By "generally targeted" the nucleic acid may target a sequence that overlaps with Pro-N-Cadherin. In particular, the nucleic acid may target a sequence in the mRNA of human Pro-N-Cadherin that is slightly longer or shorter than one of Pro-N-Cadherin, but is otherwise identical to the native form.

It is expected that perfect identity/complementarity between the nucleic acid of the invention and the target sequence, although preferred, is not essential. Accordingly, the nucleic acid of the invention may include a single mismatch compared to the mRNA of Pro-N-Cadherin. It is expected, however, that the presence of even a single mismatch is likely to lead to reduced efficiency, so the absence of mismatches is preferred. When present, 3' overhangs may be excluded from the consideration of the number of mismatches.

The term "complementarity" is not limited to conventional base pairing between nucleic acid consisting of naturally occurring ribo- and/or deoxyribonucleotides, but also includes base pairing between mRNA and nucleic acids of the invention that include non-natural nucleotides.

In one embodiment, the nucleic acid (herein referred to as double-stranded siRNA) includes the double-stranded RNA sequences for Pro-N-Cadherin.

However, it is also expected that slightly shorter or longer sequences directed to the same region of Pro-N-Cadherin mRNA will also be effective. In particular, it is expected that double-stranded sequences between 17 and 23 bp in length will also be effective.

The strands that form the double-stranded RNA may have short 3' dinucleotide overhangs, which may be DNA or RNA. The use of a 3' DNA overhang has no effect on siRNA activity compared to a 3' RNA overhang, but reduces the cost of chemical synthesis of the nucleic acid strands (Elbashir et al., 2001c). For this reason, DNA dinucleotides may be preferred.

When present, the dinucleotide overhangs may be symmetrical to each other, though this is not essential. Indeed, the 3' overhang of the sense (upper) strand is irrelevant for RNAi activity, as it does not participate in mRNA recognition and degradation (Elbashir et al., 2001a, 2001b, 2001c).

While RNAi experiments in *Drosophila* show that antisense 3' overhangs may participate in mRNA recognition and targeting (Elbashir et al. 2001c), 3' overhangs do not appear to be necessary for RNAi activity of siRNA in mammalian cells. Incorrect annealing of 3' overhangs is therefore thought to have little effect in mammalian cells (Elbashir et al. 2001c; Czauderna et al. 2003).

Any dinucleotide overhang may therefore be used in the antisense strand of the siRNA. Nevertheless, the dinucleotide is preferably —UU or -UG (or -TT or -TG if the overhang is DNA), more preferably -UU (or -TT). The -UU (or -TT) dinucleotide overhang is most effective and is consistent with (i.e. capable of forming part of) the RNA polymerase III end of transcription signal (the terminator signal is TTTTT). Accordingly, this dinucleotide is most preferred. The dinucleotides AA, CC and GG may also be used, but are less effective and consequently less preferred.

Moreover, the 3' overhangs may be omitted entirely from the siRNA.

The present disclosure also provides single-stranded nucleic acids (herein referred to as single-stranded siRNAs) respectively consisting of a component strand of one of the aforementioned double-stranded nucleic acids, preferably with the 3'-overhangs, but optionally without. The present disclosure also provides kits containing pairs of such single-stranded nucleic acids, which are capable of hybridizing with each other in vitro to form the aforementioned double-stranded siRNAs, which may then be introduced into cells.

The present disclosure also provides DNA that, when transcribed in a mammalian cell, yields an RNA (herein also referred to as an shRNA) having two complementary portions which are capable of self-hybridizing to produce a double-stranded motif or a sequence that differs from any one of the aforementioned sequences by a single base pair substitution.

The complementary portions will generally be joined by a spacer, which has suitable length and sequence to allow the two complementary portions to hybridize with each other.

The two complementary (i.e. sense and antisense) portions may be joined 5'-3' in either order. The spacer will typically be a short sequence, of approximately 4-12 nucleotides, preferably 4-9 nucleotides, more preferably 6-9 nucleotides.

Preferably the 5' end of the spacer (immediately 3' of the upstream complementary portion) consists of the nucleotides -UU- or -UG-, again preferably -UU- (though, again, the use of these particular dinucleotides is not essential). A suitable spacer, recommended for use in the pSuper system of OligoEngine (Seattle, Wash., USA) is UUCAAGAGA. In this and other cases, the ends of the spacer may hybridize with each other.

Similarly, the transcribed RNA preferably includes a 3' overhang from the downstream complementary portion. Again, this is preferably —UU or -UG, more preferably -UU.

Such shRNA molecules may then be cleaved in the mammalian cell by the enzyme DICER to yield a double-stranded siRNA as described above, in which one or each strand of the hybridized dsRNA includes a 3' overhang.

Techniques for the synthesis of the nucleic acids of the invention are of course well known in the art.

The skilled person is well able to construct suitable transcription vectors for the DNA of the present disclosure using well-known techniques and commercially available materials. In particular, the DNA will be associated with control sequences, including a promoter and a transcription termination sequence.

Of particular suitability are the commercially available pSuper and pSuperior systems of OligoEngine (Seattle, Wash., USA). These use a polymerase-III promoter (H1) and a $T_5$ transcription terminator sequence that contributes two U residues at the 3' end of the transcript (which, after DICER processing, provide a 3' UU overhang of one strand of the siRNA).

Another suitable system is described in Shin et al. (RNA, 2009 May; 15(5): 898-910), which uses another polymerase-III promoter (U6).

The double-stranded siRNAs of the present disclosure may be introduced into mammalian cells in vitro or in vivo using known techniques, as described below, to suppress expression of Pro-N-Cadherin.

Similarly, transcription vectors containing the DNAs of the present disclosure may be introduced into tumor cells in vitro or in vivo using known techniques, as described below, for transient or stable expression of RNA, again to suppress expression of Pro-N-Cadherin.

Accordingly, the present disclosure also provides a method of suppressing Pro-N-Cadherin expression in a mammalian, e.g. human, cell, the method comprising administering to the cell a double-stranded siRNA of the present disclosure or a transcription vector of the present disclosure.

Similarly, the present disclosure further provides a method of treating fibrosis, the method comprising administering to a subject a double-stranded siRNA of the invention or a transcription vector of the present disclosure.

The present disclosure further provides the double-stranded siRNAs of the present disclosure and the transcription vectors of the invention, for use in a method of treatment, preferably a method of treating fibrosis.

The present disclosure further provides the use of the double-stranded siRNAs of the present disclosure and the transcription vectors of the invention in the preparation of a medicament for the treatment of fibrosis.

The present disclosure further provides a composition comprising a double-stranded siRNA of the present disclosure or a transcription vector of the invention in admixture with one or more pharmaceutically acceptable carriers. Suitable carriers include lipophilic carriers or vesicles, which may assist in penetration of the cell membrane.

Materials and methods suitable for the administration of siRNA duplexes and DNA vectors of the present disclosure are well known in the art and improved methods are under development, given the potential of RNAi technology.

Generally, many techniques are available for introducing nucleic acids into mammalian cells. The choice of technique will depend on whether the nucleic acid is transferred into cultured cells in vitro or in vivo in the cells of a patient. Techniques suitable for the transfer of nucleic acid into mammalian cells in vitro include the use of liposomes, electroporation, microinjection, cell fusion, DEAE dextran and calcium phosphate precipitation. In vivo gene transfer techniques include transfection with viral (typically retroviral) vectors and viral coat protein-liposome mediated transfection (Dzau et al. (2003) Trends in Biotechnology 11, 205-210).

In particular, suitable techniques for cellular administration of the nucleic acids of the present disclosure both in vitro and in vivo are disclosed in the following articles:

General reviews: Borkhardt, A. 2002. Blocking oncogenes in malignant cells by RNA interference—new hope for a highly specific cancer treatment? Cancer Cell. 2:167-8. Hannon, G. J. 2002. RNA interference. Nature. 418:244-51. McManus, M. T., and P. A. Sharp. 2002. Gene silencing in mammals by small interfering RNAs. Nat Rev Genet. 3:737-47. Scherr, M., M. A. Morgan, and M. Eder. 2003b. Gene silencing mediated by small interfering RNAs in mammalian cells. Curr Med Chem. 10:245-56. Shuey, D. J., D. E. McCallus, and T. Giordano. 2002. RNAi: gene-silencing in therapeutic intervention. Drug Discov Today. 7:1040-6.

Systemic delivery using liposomes: Lewis, D. L., J. E. Hagstrom, A. G. Loomis, J. A. Wolff, and H. Herweijer. 2002. Efficient delivery of siRNA for inhibition of gene expression in postnatal mice. Nat Genet. 32:107-8. Paul, C. P., P. D. Good, I. Winer, and D. R. Engelke. 2002. Effective expression of small interfering RNA in human cells. Nat Biotechnol. 20:505-8. Song, E., S. K. Lee, J. Wang, N. Ince, N. Ouyang, J. Min, J. Chen, P. Shankar, and J. Lieberman. 2003. RNA interference targeting Fas protects mice from fulminant hepatitis. Nat Med. 9:347-51. Sorensen, D. R., M. Leirdal, and M. Sioud. 2003. Gene silencing by systemic delivery of synthetic siRNAs in adult mice. J Mol Biol. 327:761-6.

Virus mediated transfer: Abbas-Terki, T., W. Blanco-Bose, N. Deglon, W. Pralong, and P. Aebischer. 2002. Lentiviral-mediated RNA interference. Hum Gene Ther. 13:2197-201. Barton, G. M., and R. Medzhitov. 2002. Retroviral delivery of small interfering RNA into primary cells. Proc Natl Acad Sci USA. 99:14943-5. Devroe, E., and P. A. Silver. 2002. Retrovirus-delivered siRNA. BMC Biotechnol. 2:15. Lori, F., P. Guallini, L. Galluzzi, and J. Lisziewicz. 2002. Gene therapy approaches to HIV infection. Am J Pharmacogenomics. 2:245-52. Matta, H., B. Hozayev, R. Tomar, P. Chugh, and P. M. Chaudhary. 2003. Use of lentiviral vectors for delivery of small interfering RNA. Cancer Biol Ther. 2:206-10. Qin, X. F., D. S. An, I. S. Chen, and D. Baltimore. 2003. Inhibiting HIV-1 infection in human T cells by lentiviral-mediated delivery of small interfering RNA against CCRS. Proc Natl Acad Sci USA. 100:183-8. Scherr, M., K. Battmer, A. Ganser, and M. Eder. 2003a. Modulation of gene expression by lentiviral-mediated delivery of small interfering RNA. Cell Cycle. 2:251-7.

Shen, C., A. K. Buck, X. Liu, M. Winkler, and S. N. Reske. 2003. Gene silencing by adenovirus-delivered siRNA. FEBS Lett. 539:111-4.

Peptide delivery: Morris, M. C., L. Chaloin, F. Heitz, and G. Divita. 2000. Translocating peptides and proteins and their use for gene delivery. Curr Opin Biotechnol. 11:461-6. Simeoni, F., M. C. Morris, F. Heitz, and G. Divita. 2003. Insight into the mechanism of the peptide-based gene delivery system MPG: implications for delivery of siRNA into mammalian cells. Nucleic Acids Res. 31:2717-24. Other technologies that may be suitable for delivery of siRNA to the target cells are based on nanoparticles or nanocapsules such as those described in U.S. Pat. Nos. 6,649,192B and 5,843,509B.

In therapeutic applications, agents capable of inhibiting the action of Pro-N-Cadherin or agents capable of preventing or reducing the expression of Pro-N-Cadherin are preferably formulated as a medicament or pharmaceutical together with one or more other pharmaceutically acceptable ingredients well known to those skilled in the art, including, but not limited to, pharmaceutically acceptable carriers, adjuvants, excipients, diluents, fillers, buffers, preservatives, anti-oxidants, lubricants, stabilizers, solubilizers, surfactants (e.g., wetting agents), masking agents, coloring agents, flavoring agents, and sweetening agents.

The term "pharmaceutically acceptable" as used herein pertains to compounds, ingredients, materials, compositions, dosage forms, etc., which are, within the scope of sound medical judgment, suitable for use in contact with the tissues of the subject in question (e.g., human) without excessive toxicity, irritation, allergic response, or other problem or complication, commensurate with a reasonable benefit/risk ratio. Each carrier, adjuvant, excipient, etc. must also be "acceptable" in the sense of being compatible with the other ingredients of the formulation.

Suitable carriers, adjuvants, excipients, etc. can be found in standard pharmaceutical texts, for example, Remington's Pharmaceutical Sciences, 18th edition, Mack Publishing Company, Easton, Pa., 1990; and Handbook of Pharmaceutical Excipients, 2nd edition, 1994.

The formulations may be prepared by any methods well known in the art of pharmacy. Such methods include the step of bringing into association the active compound with a carrier which constitutes one or more accessory ingredients. In general, the formulations are prepared by uniformly and intimately bringing into association the active compound with carriers (e.g., liquid carriers, finely divided solid carrier, etc.), and then shaping the product, if necessary.

The formulations may be prepared for topical, parenteral, systemic, intravenous, intra-arterial, intramuscular, intrathecal, intraocular, intra-conjunctival, subcutaneous, oral or transdermal routes of administration which may include injection. Injectable formulations may comprise the selected agent in a sterile or isotonic medium.

Administration is preferably in a "therapeutically effective amount", this being sufficient to show benefit to the individual. The actual amount administered, and rate and time-course of administration, will depend on the nature and severity of the disease being treated. Prescription of treatment, e.g. decisions on dosage etc., is within the responsibility of general practitioners and other medical doctors, and typically takes account of the disorder to be treated, the condition of the individual patient, the site of delivery, the method of administration and other factors known to practitioners. Examples of the techniques and protocols mentioned above can be found in Remington's Pharmaceutical Sciences, 20th Edition, 2000, pub. Lippincott, Williams & Wilkins.

In some embodiments, kits for carrying out the methods described herein are provided. The kits provided may contain the necessary components with which to carry out one or more of the above-noted methods. In one embodiment, a kit for detecting a biomarker specific for pathological fibroblast cells are provided. The kit may comprise an antibody specific to the biomarker. In a preferred embodiment, the biomarker is pro-N-cadherin. In some embodiments, the detecting is by an antibody specific to the biomarker. In other embodiments, the detecting is by other methods described herein. In one embodiment, the kit comprises an antibody to pro-N-cadherin conjugated to a detection agent or magnetic beads. In further embodiments, a control is provided. In one embodiment, the control is a positive control, for example, a sample positive for the biomarker specific for the fibroblast cells expressing pro-N-cadherin. In another example, the control is a control obtained from a healthy individual that does not have such pathological fibroblast cells.

In further embodiments, the kits may include a composition for the treatment of a subject in which pathological fibroblast cells have been detected. The kits may include an antibody specific to the biomarker (e.g. pro-N-cadherin antibody). In some further embodiments, the kit may further include one or more additional therapeutic agents (e.g., therapeutic agents for treating fibrosis or conditions associated with pathological fibroblast cells).

One of ordinary skill in the art will readily recognize that the foregoing represents merely a detailed description of certain preferred embodiments of the present invention. Various modifications and alterations of the compositions and methods described above can readily be achieved using expertise available in the art and are within the scope of the invention.

EXAMPLES

The following examples are illustrative, but not limiting, of the compounds, compositions, and methods of the present invention. Other suitable modifications and adaptations of the variety of conditions and parameters normally encountered in clinical therapy and which are obvious to those skilled in the art are within the spirit and scope of the invention.

Example I

This example describes the expression of Pro-N-cadherin on the cell surface of fibroblasts isolated from tissues pathological in origin but not expressed on the cell surface of fibroblasts isolated from non-diseased tissues.

Figure 1A:
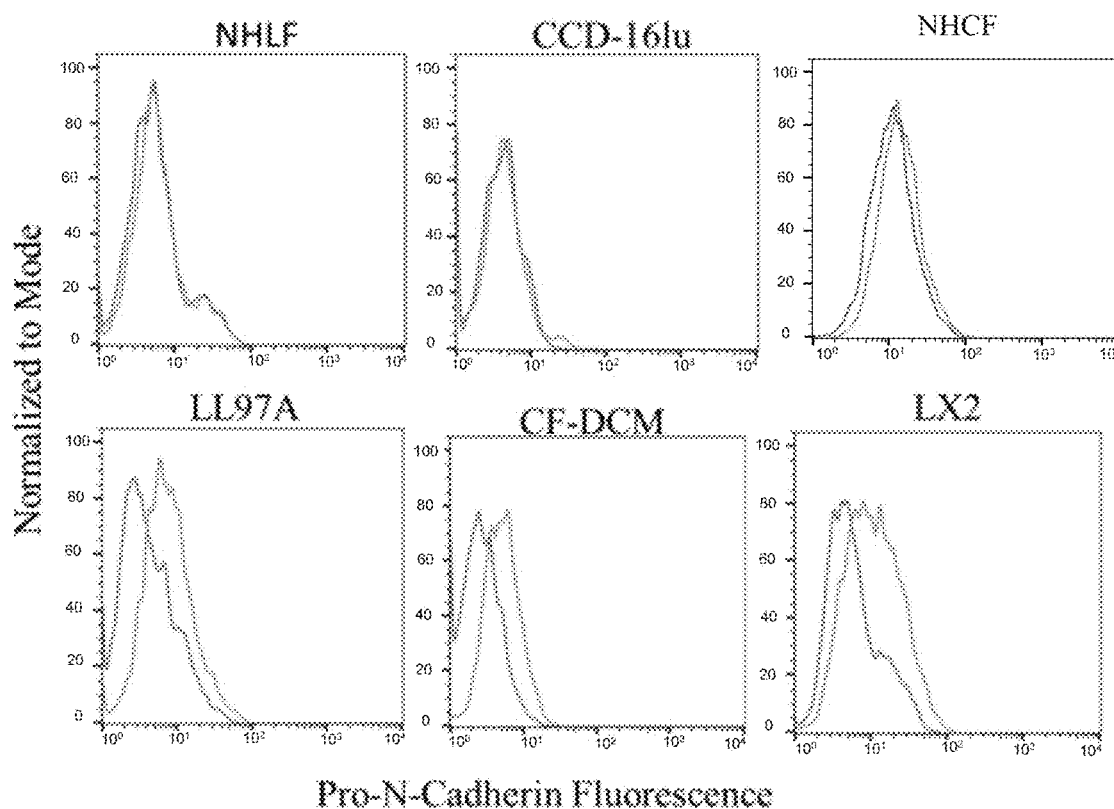
Figure 1B:
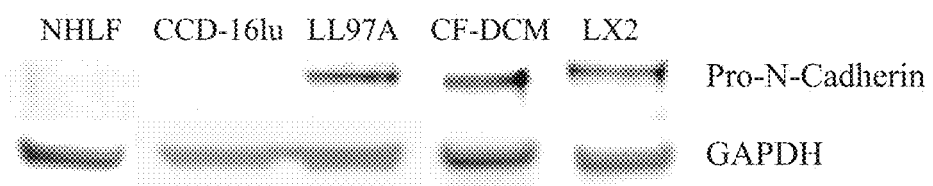

A murine monoclonal antibody (mAb) was obtained from the University of Nebraska Medical School. This antibody is highly specific for the precursor (pro) domain of Pro-N-cadherin (see, Wahl, J. K., et al Journal of Biological Chemistry, 2003. 278(19): p. 17269-17276). Western blot analysis shows that this mAb recognizes Pro-N-cadherin protein from human pathological fibroblasts from lung (LL97A), heart (CF-DCM) and liver (LX2) with no protein expression detected in normal fibroblasts NHLF and CCD-161u (FIG. 1B) due to normal N-cadherin protein processing. Aberrant cell surface localization of Pro-N-cadherin is demonstrated by flow cytometry analyzed pathological fibroblasts from lung (LL97A), heart (CF-DCM) and liver (LX2) with no cell surface localization of Pro-N-cadherin detected on normal fibroblasts NHLF, CCD-161u, or NHCF (FIG. 1A). FIGS. 4, 5 and 6 are images of Pro-N-cadherin cell surface localization on pathological fibroblasts LL97A. Collectively, this data demonstrates that Pro-N-cadherin is a suitable biomarker for identifying pathological fibroblasts.

Example II

This example demonstrates that mAb treatment targeting the pro-domain of the precursor N-cadherin results in reduction of proliferation, activation and viability of pathological fibroblasts. This example also demonstrates the phenomenon defined as the hook effect (Also known as the prozone effect) related to monoclonal antibodies.

Figure 1C:
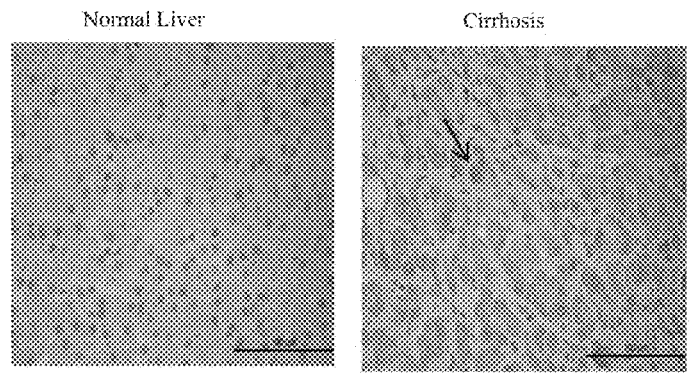
Figure 1C:
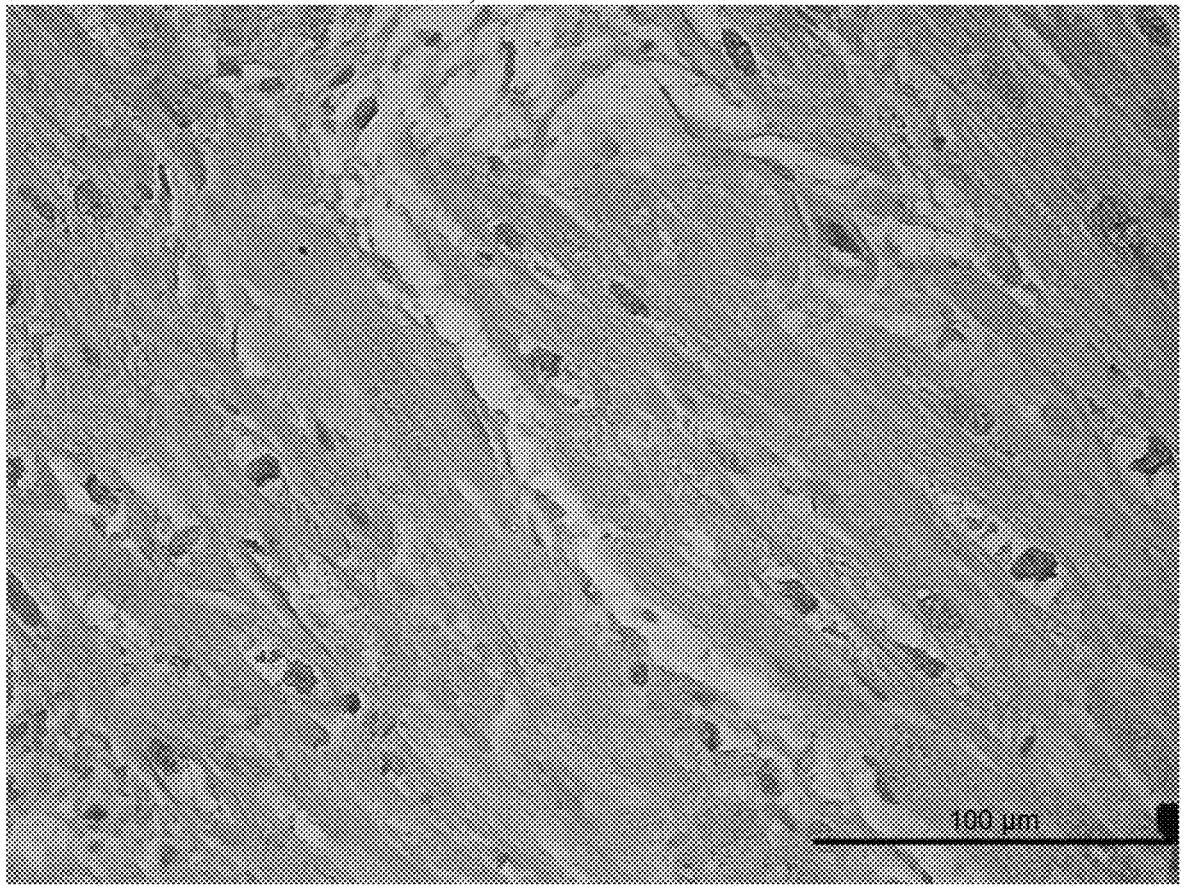
Figure 2:
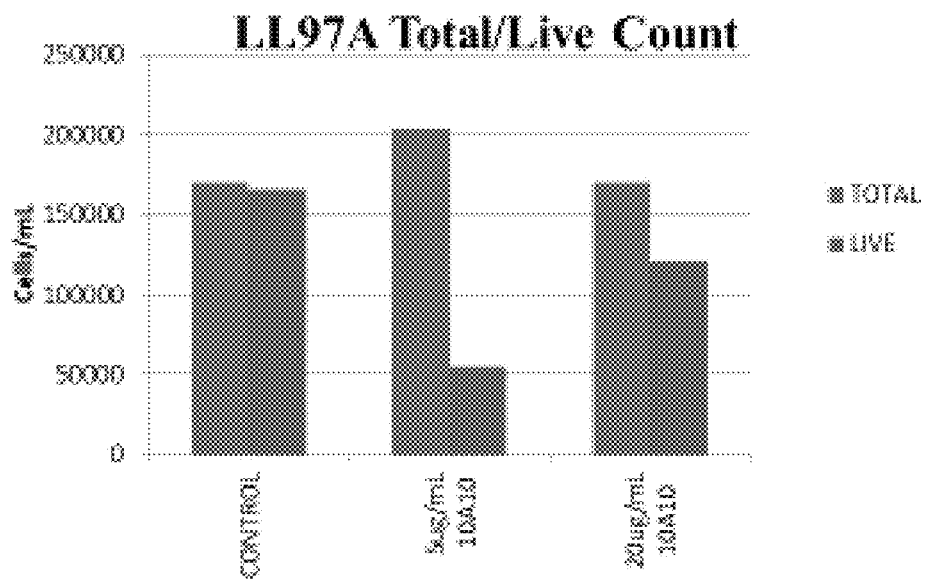
FIG. 2: Pro-N-Cadherin MAb is cytotoxic to fibroblast isolated from idiopathic pulmonary fibrosis. LL97A fibroblasts were plated at $1 \times 10^3$ cells/well in 96-well plates and allowed to anchor overnight. Cells were treated with Pro-N-cadherin antibody 10A10 overnight, lifted with trypsin, pooling 6-wells per condition. Cells were then stained with trypan blue and counted using the Bio-rad TC 20 automated cell counter.
Figure 2:
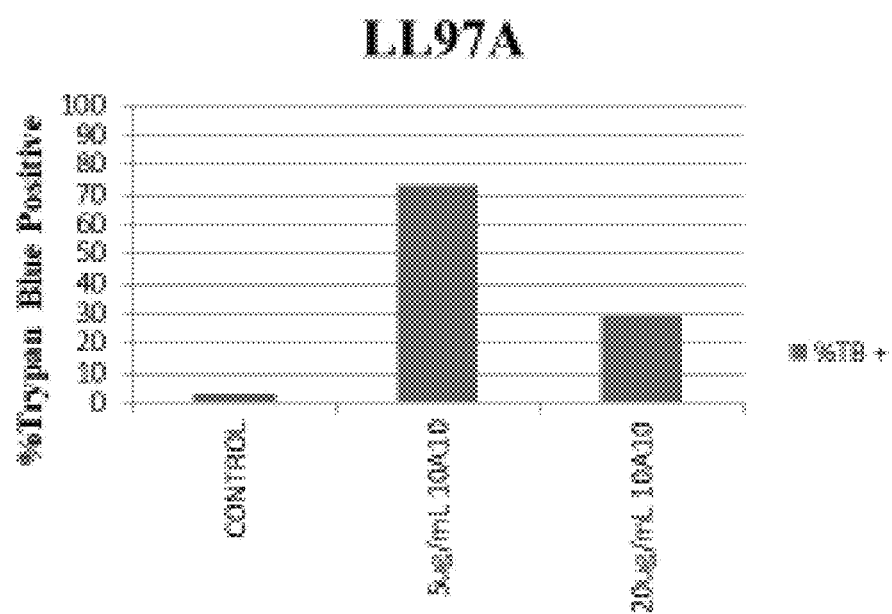
Figure 3A:
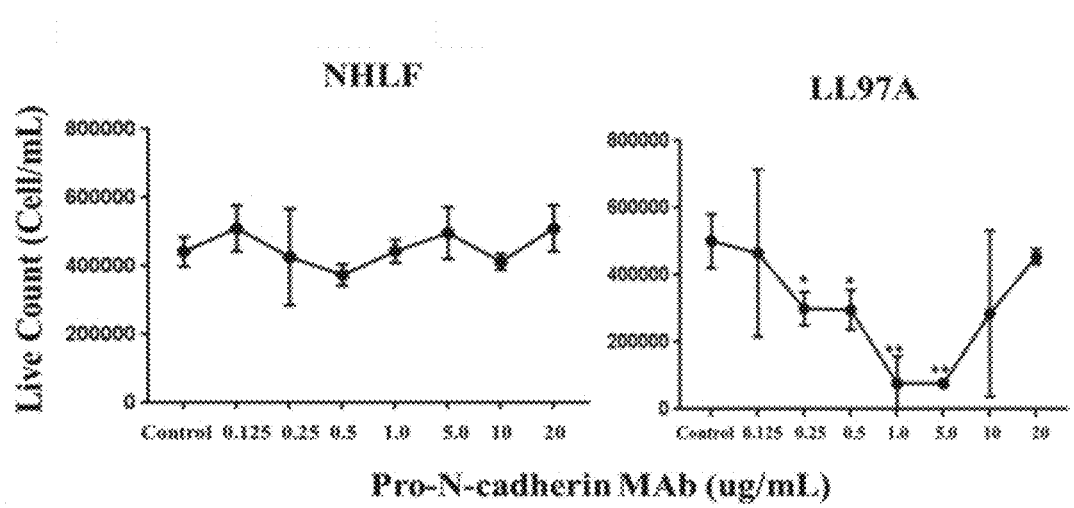
FIG. 3A-J: Significantly reduced viable cell numbers and proliferation of pathological myofibroblasts as a result of pro-N-cadherin mAb treatment at various concentrations. A. Overnight treatment with pro-N-cadherin mAb had no effect on NHLF viable cell numbers but significantly reduced LL97A IPF myofibroblasts. B. Effects on proliferation from overnight treatment with pro-N-cadherin mAb of CF-DCM and LX2 myofibroblasts was analyzed by relative BrdU amount incorporation into newly synthesized DNA. C. Short duration (1 Hr) and time course (0.5-2 Hr) treatment of cardiac myofibroblasts from DCM and IPF myofibroblasts respectively with pro-N-cadherin mAb. LDH activity from the supernatants was used as a marker of cell membrane permeablization and generalized cell death of myofibroblasts. D. CF-DCM were assessed for cell surface pro-N- cadherin by flow cytometry after overnight pro-N-cadherin mAb treatment [0.625 ug/mL] and compared to non-treated control. E. LX2 hepatic stellate myofibroblasts α-SMA gene expression measured by rt-PCR after overnight pro-N-cadherin mAb [2 ug/mL] treatment relative to controls and normalized to GAPDH. Representative data from two different pro-N-cadherin mAbs. F. LL97A α-SMA gene expression measured by rt-PCR after overnight pro-N-cadherin mAb [2 ug/mL] treatment relative to controls and normalized to GAPDH. G. LX2 cells were plated at $1\times10^3$ cells/well in 96-well plates and allowed to anchor overnight. Cells were treated with Pro-N-cadherin antibody 10A10 overnight and lifted with trypsin. For each condition, 3 wells were pooled together for each count. Cells were then stained with trypan blue and counted using the Bio-rad TC 20 automated cell counter. H. Primary cardiac fibroblasts from explant tissue were plated at $1\times10^3$ cells/well in a 96-well plate. Cells were treated with Pro-N-cadherin antibody 19D8 overnight and lifted with trypsin. Cells were then stained with trypan blue and counted using the Bio-rad TC 20 automated cell counter. I. Primary cardiac fibroblasts from explant tissue were plated at $1\times10^3$ cells/well in a 96-well plate. Cells were treated with Pro-N-cadherin antibody 19D8 overnight for 3 nights replacing the media and antibody each day. Cells were then trypsinized and stained with trypan blue and counted using the Bio-rad TC 20 automated cell counter. J. LL97A cells were plated at $1\times10^3$ cells/well in 96-well plates and allowed to anchor overnight. Cells were treated with Pro-N-cadherin antibody 10A10 and BrdU overnight. BrdU incorporation was measured following the manufacturer's protocol (Millipore Sigma 11647229001).
Figure 3B:
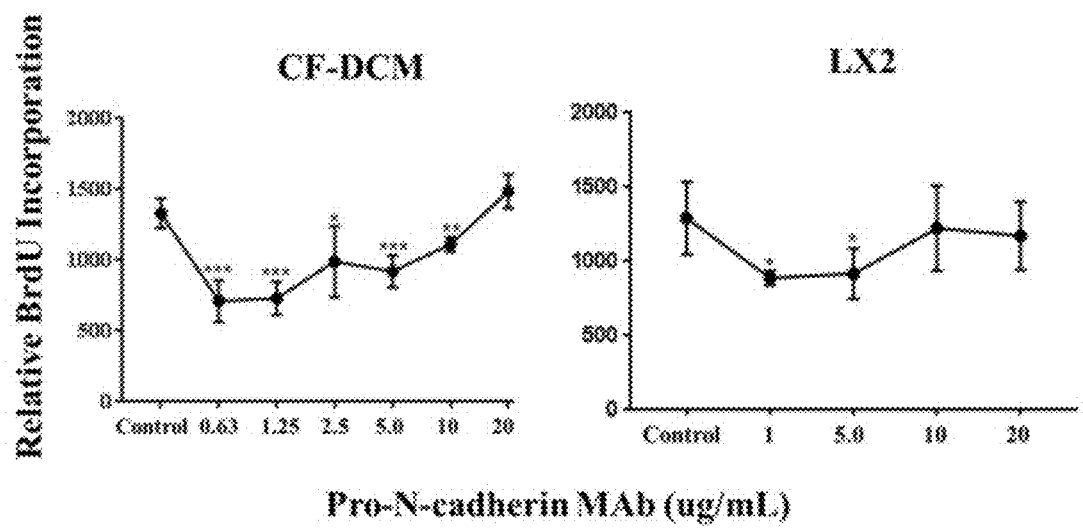
Figure 3C:
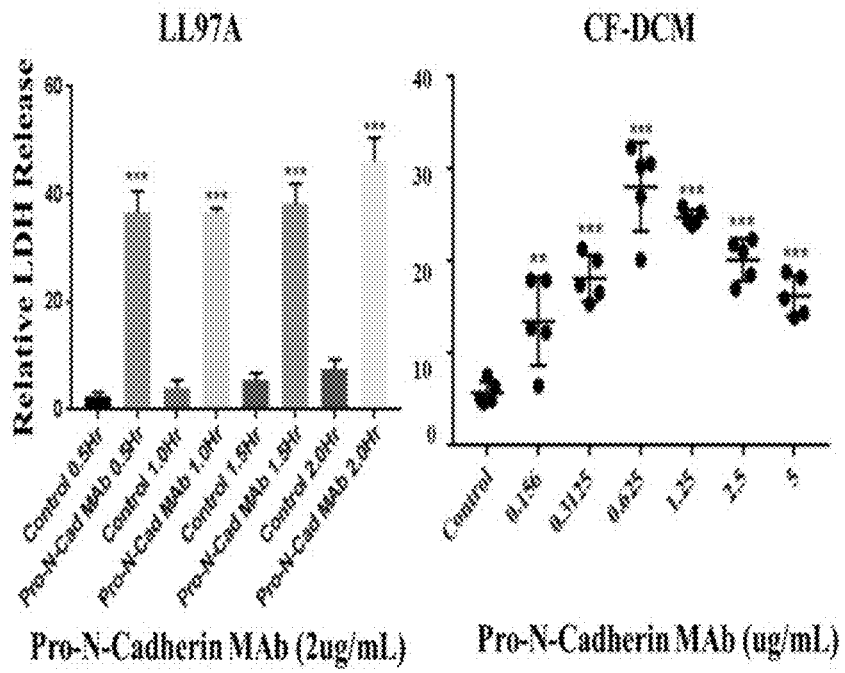
Figure 3D:
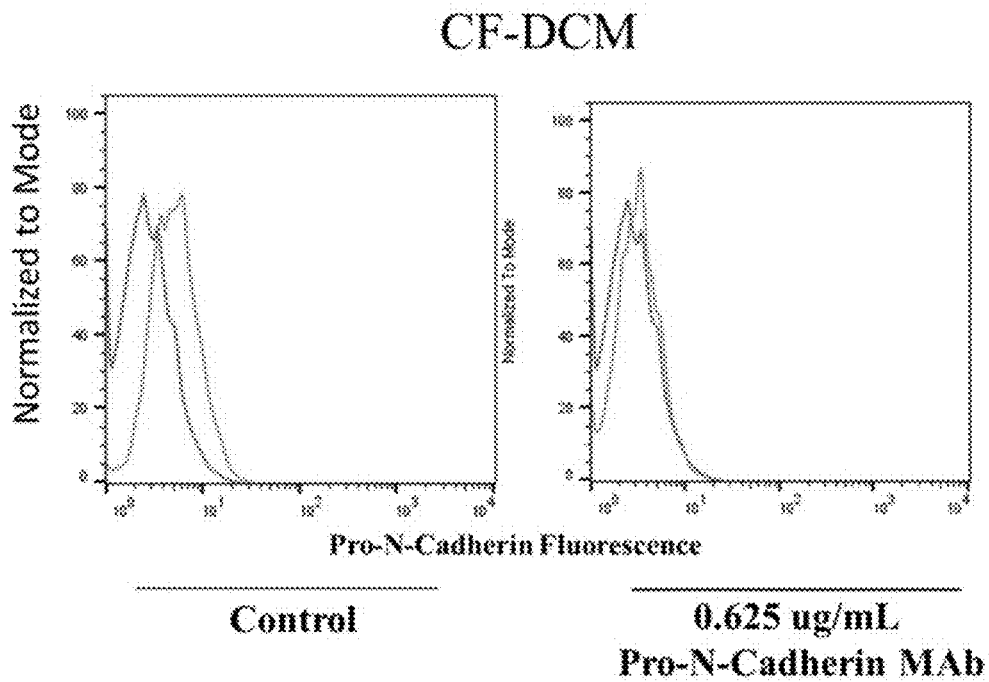
Figure 3E:
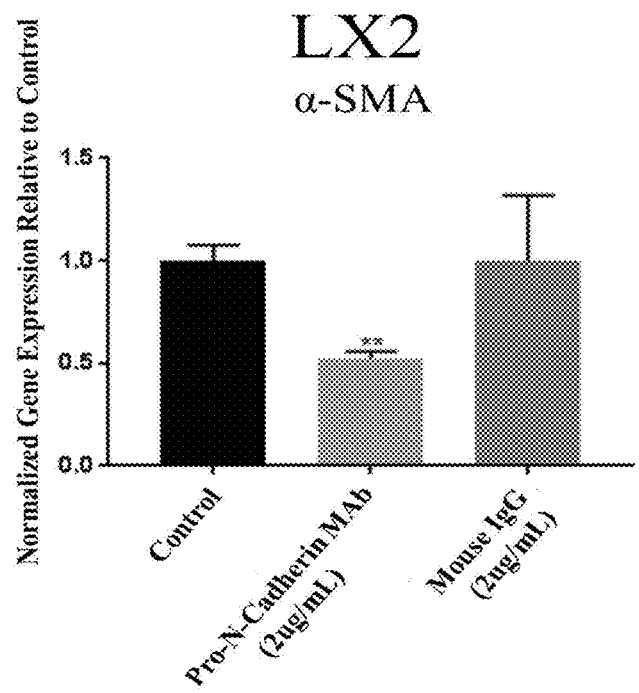
Figure 3F:
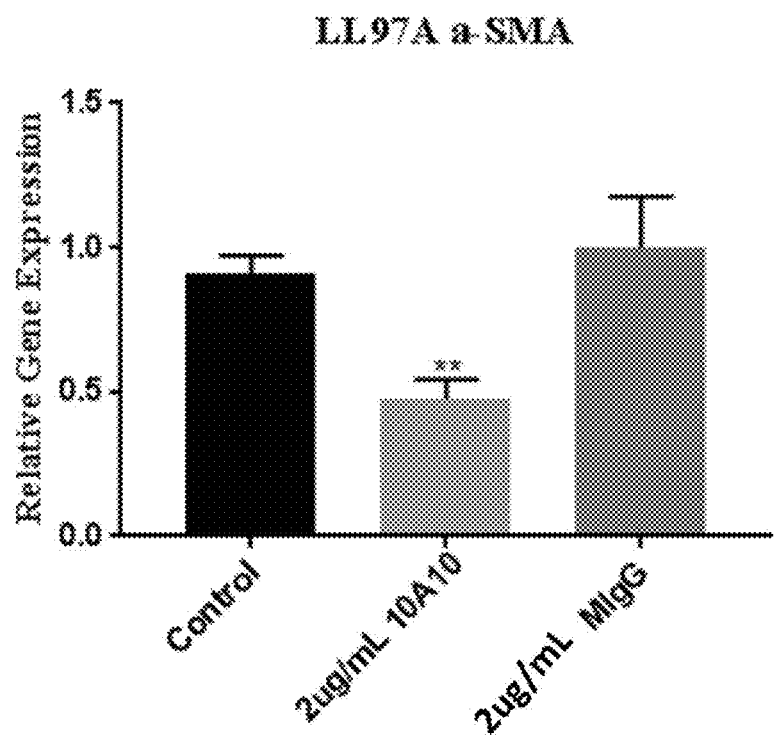
Figure 3G:
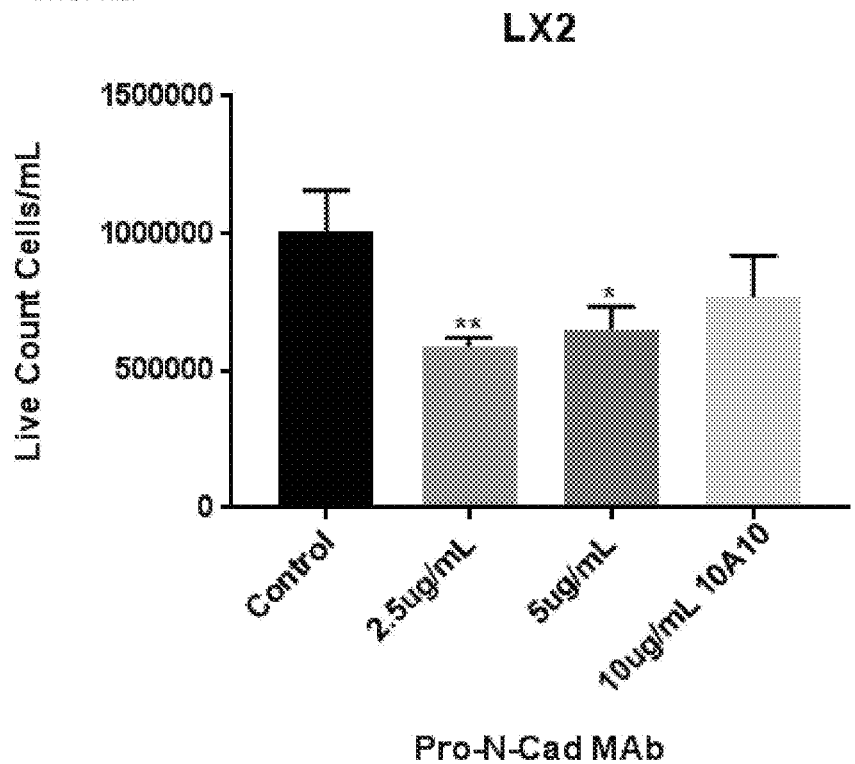

To assess whether administering an antibody against the Pro-N-cadherin protein can result in cell death, LL97A diseased fibroblasts were treated with monoclonal antibody (10A10), that specifically targets the pro domain of the precursor N-cadherin molecule. Administration of the 10A10 antibody resulted in cell death of approximately seventy-five percent of the fibroblast population overnight, confirmed by trypan blue staining (FIG. 2). FIG. 2 demonstrates reduced viability of pathological LL97A fibroblasts with Pro-N-cadherin treatment. Pathological fibroblasts from heart, lung and liver were challenged with Pro-N-cadherin mAb and effects were measured by proliferation assays, flow cytometry, cytotoxicity assays, dose titrations and time course in vitro (FIG. 3). FIGS. 3B, 3J, and 3G demonstrates reduced DNA synthesis by BrdU incorporation by pathological fibroblasts and reduced live cell number when treated with Pro-N-cadherin mAb, indicative of cell death and reduced proliferation. Decreased cell viability with Pro-N-cadherin mAb treatment of pathological fibroblasts was demonstrated by measuring LDH release (FIG. 1C). Significantly reduced α-SMA gene expression was also observed after LX2 and LL97A cells were treated with Pro-N-cadherin mAb overnight (FIG. 3E and FIG. 3F), demonstrating reduction in fibroblast activation state. Dose titrations of the monoclonal antibodies revealed the hook effect on each pathological fibroblast culture tested by proliferation and cytotoxicity assays (FIGS. 3A, B&C). FIG. 3 demonstrates the hook effect, in which the epitope is saturated by competitive binding of the mAb at high monoclonal antibody concentrations. The hook effect is a well characterized phenomenon, exclusively indicative of monoclonal antibody activity (see, Caron, P. C., et al., Cancer, 1994. 73(S3): p. 1049-1056; Taborda, C. P., et al., The Journal of Immunology, 2003. 170(7): p. 3621-3630). In this case, when the epitope is saturated, steric hindrance limits antibody-antigen interactions to monovalent binding that limits crosslinking of the Pro-N-cadherin antigen and decreases efficacy. At optimal concentrations, the antibody binds bivalently and optimal efficacy of cytotoxicity and reduced proliferation is observed.

Example III

This example demonstrates that the biological effects of targeting Pro-N-cadherin is limited to fibroblasts from pathological conditions without effecting non-pathological fibroblasts.

To demonstrate the specificity of targeting Pro-N-cadherin, primary lung fibroblasts isolated from non-diseased tissue were treated with Pro-N-cadherin mAb and compared to treated fibroblasts isolated from fibrotic lung (FIG. 1A). FIG. 1A demonstrates no effect on live cell number of Pro-N-cadherin mAb treated NHLF. In contrast, FIG. 1A demonstrates significant reduction of live cell number of Pro-N-cadherin mAb treated LL97A. This demonstrates specificity of targeting Pro-N-cadherin is limited to pathological fibroblasts.

Example IV

This example demonstrates that pathological fibroblasts defined by cell surface Pro-N-cadherin expression can be eliminated from the total pool of fibroblasts by targeting Pro-N-cadherin.

Figure 3H:
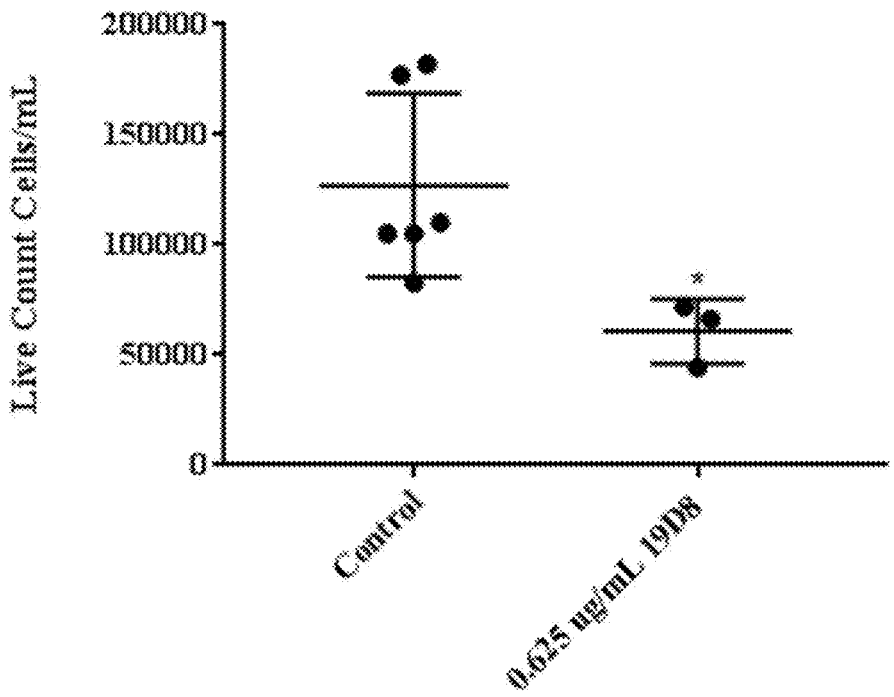
Figure 3I:
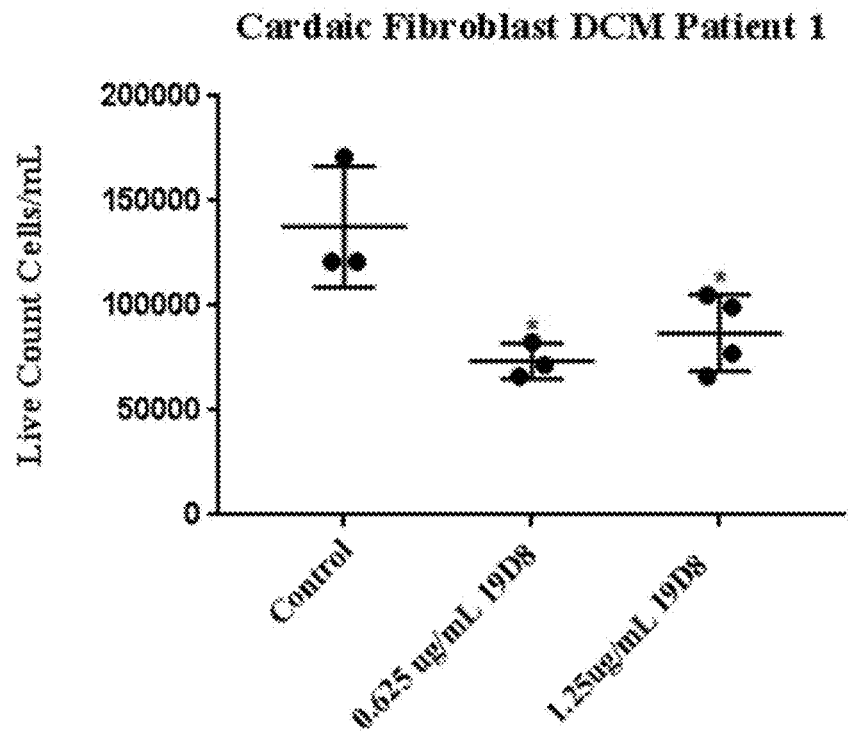
Figure 3J:
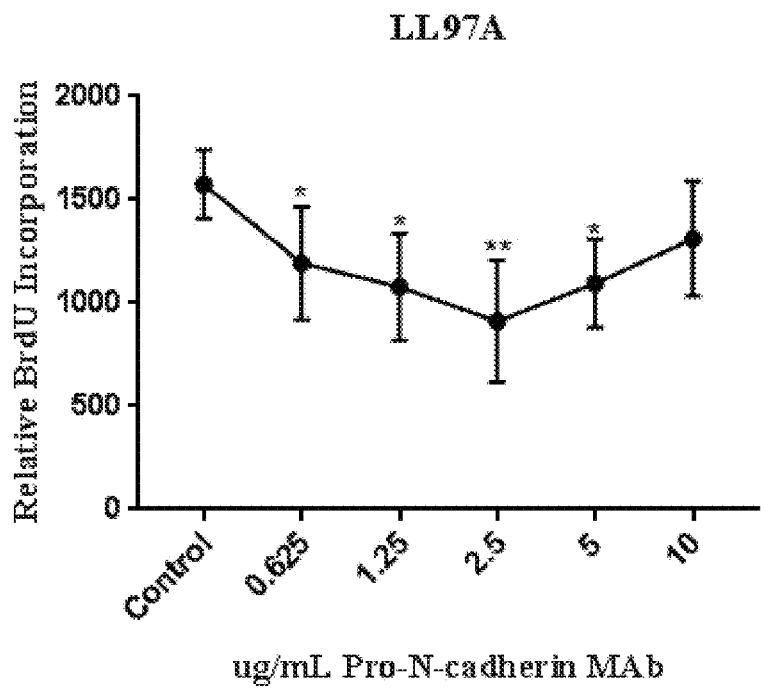

FIG. 3H demonstrates the reduction in live cell number of pathological fibroblasts CF-DCM after overnight treatment with Pro-N-cadherin mAb. FIG. 3I shows similar reduction in live cell number of pathological fibroblasts CF-DCM after three consecutive nights of overnight treatment with Pro-N-cadherin mAb. To assess the population of fibroblasts remaining after overnight treatment of CF-DCM with optimal mAb concentration, the pathological subpopulation of fibroblasts can no longer be detected by measuring cell surface Pro-N-cadherin of the remaining fibroblast culture via flow cytometry (FIG. 3D), demonstrating the elimination of pathological fibroblasts from the total pool of fibroblasts.

Example V

In conjunction with example I, this example demonstrates that pathological fibroblasts expressing cell surface Pro-N-cadherin are present in human tissues pathological in origin but not normal human tissue.

Immunohistochemistry confirmed Pro-N-cadherin protein expression in patient tissue derived from cirrhotic liver and fatty liver but not normal liver (FIG. 1C and FIG. 1E). Immunohistochemistry confirmed Pro-N-cadherin protein expression in patient tissue derived from explanted heart from patient with dilated cardiomyopathy (FIG. 1F circles indicate interstitial fibroblasts) but not normal human atrial tissue trimmings from implanted heart (FIG. 1D and FIG. 1F). This demonstrates aberrant processing of N-cadherin protein and presence of Pro-N-cadherin protein expression in human patient derived pathological tissues.

Example VI

This example provides the materials and methods utilized in Examples I-V.

Cell Culture and Biochemical Assays

All cells were cultured at 37 C, 5% CO2 in a humidified chamber. The LL97A (ATCC CCL-191) and CCD-16Lu (ATCC CCL-204) cell lines were purchased from ATCC and grown by their specifications. Primary ventricular normal human cardiac fibroblasts (NHCF) were purchased from Lonza (CC-2904) and grown in DMEM (Millipore Sigma F4135) supplemented with 10% FBS and 1× PenStrep (Gibco 15140122). Ventricular cardiac fibroblasts from explant human tissue were received from Duke Human Heart Repository (IRB # Pro87831) and grown in DMEM; 10% FBS; 1× PenStrep. Primary normal human lung fibroblasts (NHLF) were purchased from the Duke Cell Culture Facility (Lonza CC-2512) and grown in DMEM; 10% FBS; 1× PenStrep. Hepatic stellate myofibroblast cell line LX2 was gifted by the Diehl Laboratory at Duke and grown in DMEM; 10% FBS; 1× PenStrep. Lactate dehydrogenase cytotoxicity (LDH) and BrdU assays were performed using kits Millipore Sigma cat # MAK066 and MilliporeSigma cat #11647229001, respectively, following the manufacturer's protocol. For cell counting experiments, cells were trypsinized, stained with trypan blue (ThermoFisher 15250061), and counted using the Bio-Rad TC20 automated cell counter.

Pro-N-Cadherin Antibody Purification

Pro-N-cadherin monoclonal antibody-producing hybridomas 10A10 and 19D8 were received from University of Nebraska, acclimated to Hybridoma-SFM (Gibco 12045076), and grown to confluency. Supernatant was collected by centrifugation and antibodies were batch purified by affinity chromatography using protein G sepharose (GE 17061801) following the manufacturer's protocol. Antibodies were dialyzed into final buffer PBS pH 7.4 for these studies.

Tissue Processing

Left ventricular, explant cardiac tissues were received from the Duke Human Heart Repository within 12 hours of explant in PBS pH 7.4 1× pen strep (Gibco 15140122), on ice and processed same day. Tissues were divided and fixed overnight at room temperature in 4% paraformaldehyde PBS pH 7.4 followed by 70% EtOH and embedded in paraffin or immediately processed for fibroblast isolation. Liver tissues were provided by Diehl lab at Duke University embedded in paraffin.

Fibroblast Isolation from Explant Tissues

Tissues were minced into small pieces and incubated in appropriate volume of tissue dissociation solution, PBS pH 7.4, 5 mg/mL Collagenase Type IV (Gibco 17104019), 1.3 mg/mL Dispase II (Gibco 17105041), 0.05% Trypsin, with agitation at 37 Celsius for 1 hour. After incubation in dissociation solution, 25 mL of HBSS (Gibco 14175-095) was added, followed by serial pipetting for manual dissociation and centrifugation at 1,200 RPM, 4 C, for 10 minutes. The supernatant was then aspirated and the pellet was resuspended in 5 mL HBSS then passed through 100 micron filter followed by a 70 micron filter. The solution was then centrifuged at 1,200 RPM, 4 C, for 5 minutes, aspirating the supernatant and resuspending pellet into DMEM; 10% FBS; 1× Pen Strep. Cells were plated overnight and passaged to remove blood and myocyte contaminant.

IHC

Immunohistochemical detection of pro-N-cadherin was performed on formalin fixed paraffin embedded tissue samples sectioned at 3-5 microns. Sections were deparaffinated with xylene, rehydrated, and treated with 3% $H_2O_2$ to quench endogenous peroxidase. Heat-mediated antigen retrieval was performed in a citrate buffer pH=6, and blocked with 5% horse serum. Pro-N-cadherin was detected using purified 10A10 antibody at 5-10 ug/ml at 4 C overnight. An avidin-biotin amplification step and chromogenic detection (DAB) of anti-mouse HRP-conjugated secondary antibody was used to visualize pro-N-cadherin localization and expression. Tissues were counter-stained with Mayer's hematoxylin and mounted with Cytoseal 60 (ThermoFisher 8310-4) mounting media for imaging.

SDS-PAGE and Immunoblotting

Cell lysates were prepared using RIPA buffer (Sigma R0278) supplemented with Halt Protease & Phosphatase Inhibitor Cocktail (ThermoFisher 1861284) and Benzonase (Millipore Sigma E8263). Protein concentration of each lysate was measured using Pierce BCA protein assay (ThermoFisher 23225). Precleared lysates were boiled in sample buffer (ThermoFisher NP0007) and 50 µg of protein was loaded onto 10% NuPage gels containing 0.1% SDS under reducing conditions. A discontinuous Laemmli buffer system was used. The proteins were transferred from the gels to nitrocellulose membranes. The molecular weights were assessed using Precision Plus Prestained Marker (Bio-Rad 1610373). The membranes were thoroughly washed with tris-buffered saline (TBS) and then blocked with infrared blocking buffer (Rockland MB-070) for 1 hour at room temperature. Membranes were incubated with 1:5000 Pro-N-cadherin 10A10 antibody, GAPDH antibody (Santa Cruz sc-32233), Lactase Dehydrogenase antibody (Abcam AB47010), or Furin antibody (Abcam AB3467) overnight at 4 C. After incubation with the primary antibody, the membranes were washed 3 times for 5 min each with TBS containing 0.1% Tween 20 (TBST). The membranes were then incubated with a 1:10,000 dilution of appropriate Alexa Fluor conjugated secondary. The membranes were washed twice for 5 min each with TBST and once with TBS for 5 min. The probed membranes were scanned on a Li-Cor Odyssey System (Li-Cor Biosciences, Lincoln, Nebr.).

Flow Cytometry

Cells were plated in complete media in 10 cm dishes and allowed to anchor overnight. The following day, cells were washed with PBS pH 7.4, then detached using PBS pH 7.4; 2 mM EDTA at 37 C for approximately 5 minutes. Cells were kept on ice for the duration of the staining procedure. Cells were pelleted at 1,200 RPM, 4 C, for 5 minutes followed by supernatant aspiration, PBS pH 7.4 wash, and resuspension in PBS pH 7.4; 1% BSA. Approximately $1\times10^6$ cells/mL were used for each condition. Cells were incubated with either 10A10 or 19D8 Pro-N-cadherin antibody (5 ug/mL) for 30 minutes, or 5 ug/mL mouse IgG1 isotype control (R&D Systems MAB002). Cells were washed with PBS pH 7.4; 1% BSA followed by 5 ug/mL Alexa Fluor 488 secondary antibody (ThermoFisher A11029) incubation for 30 minutes. Cells were then washed with PBS pH 7.4; 1% BSA and stained with 7AAD (BioLegend 420403) following the manufacturer's protocol. Cells were analyzed using the Guava EasyCyte flow cytometer and the latest version of Flowjo software, gating and excluding 7AAD positive cells.

Immunofluorescent Microscopy

For immunofluorescent imaging, LL97A cells were plated into 8-well chamber slides ($5\times10^4$ cells/well) and allowed to adhere overnight. Each well was aspirated, washed with PBS pH 7.4 and fixed in 4% formaldehyde for 15 minutes at room temperature. Cells were then permeabilized with 0.1% Triton; PBS pH 7.4 for 30 minutes at room temperature, and blocked with 5% goat serum (Abcam AB7481); PBS pH 7.4 for 1 hour at room temperature. Primary antibody against Pro-N-cadherin, 19D8, was incubated at 5 ug/mL on cells for 1 hour at room temperature followed by AlexaFluor488 conjugated secondary for 1 hour at room temperature. Cells were stained with AlexaFluor594 Phalloidin (Life Technologies A12381) and DAPI (Sigma D9542) following manufacturer's protocol. Slides were allowed to dry and cover slips were mounted using ProLong Gold (Invitrogen 43110) according to manufacturer's protocol. Images were taken using the Leica DMI400 B, using the 60× oil immersion objective with 10× ocular objective. All images are 600×.

Statistical Analysis

Statistical analysis was performed using the latest version of GraphPad Prism software (*$P<0.05$, $P<0.01$, *$P<0.001$).

INCORPORATION BY REFERENCE

The entire disclosure of each of the patent documents and scientific articles referred to herein is incorporated by reference for all purposes.

EQUIVALENTS

The invention may be embodied in other specific forms without departing from the spirit or essential characteristics thereof. The foregoing embodiments are therefore to be considered in all respects illustrative rather than limiting the invention described herein. Scope of the invention is thus indicated by the appended claims rather than by the foregoing description, and all changes that come within the meaning and range of equivalency of the claims are intended to be embraced therein.

---

---

What is claimed is:

1. A method of characterizing a sample, the method comprising:
    a) assaying for the presence of fibroblast cells expressing pro-N-cadherin in a sample obtained from a human subject; and
    b) characterizing the sample as i) having pathological fibroblast cells if the presence of fibroblast cells expressing pro-N-cadherin are detected in the assaying step, or ii) not having pathological fibroblast cells if the presence of fibroblast cells expressing pro-N-cadherin are not detected in the assaying step,
    wherein a presence of pathological fibroblast cells indicates the subject is experiencing fibrosis and/or a condition associated with fibrosis selected from:
    respiratory conditions selected from pulmonary fibrosis, cystic fibrosis, idiopathic pulmonary fibrosis, progressive massive fibrosis, scleroderma, obliterative bronchiolitis, Hermansky-Pudlak syndrome, asbestosis, silicosis, chronic pulmonary hypertension, AIDS associated pulmonary hypertension, sarcoidosis, tumor stroma in lung disease, and asthma;
    chronic liver diseases selected from primary biliary cirrhosis (PBC), schistosomal liver disease, and liver cirrhosis;
    cardiovascular conditions selected from hypertrophic cardiomyopathy, dilated cardiomyopathy (DCM), fibrosis of the atrium, atrial fibrillation, fibrosis of the ventricle, ventricular fibrillation, myocardial fibrosis, Brugada syndrome, myocarditis, endomyocardial fibrosis, myocardial infarction, fibrotic vascular disease, hypertensive heart disease, arrhythmogenic right ventricular cardiomyopathy (ARVC), tubulointerstitial and glomerular fibrosis, atherosclerosis, varicose veins, and cerebral infarcts;
    neurological conditions selected from gliosis and Alzheimer's disease;
    Duchenne muscular dystrophy (DMD);
    Becker's muscular dystrophy (BMD);
    gastrointestinal conditions selected from Crohn's disease, microscopic colitis and primary sclerosing cholangitis (PSC);
    skin conditions selected from scleroderma, nephrogenic systemic fibrosis and cutis keloid;
    arthrofibrosis;

Dupuytren's contracture;
mediastinal fibrosis;
retroperitoneal fibrosis;
myelofibrosis;
Peyronie's disease;
adhesive capsulitis;
kidney diseases selected from renal fibrosis, nephritic syndrome, Alport's syndrome, HIV associated nephropathy, polycystic kidney disease, Fabry's disease, diabetic nephropathy, chronic glomerulonephritis, and nephritis associated with systemic lupus;
progressive systemic sclerosis (PSS);
chronic graft versus host disease;
diseases of the eye selected from Grave's ophthalmopathy, epiretinal fibrosis, retinal fibrosis, subretinal fibrosis associated with macular degeneration, wet age-related macular degeneration (AMD), diabetic retinopathy, glaucoma, corneal fibrosis, post-surgical fibrosis of the posterior capsule following cataract surgery, post-surgical fibrosis of the bleb following trabeculectomy for glaucoma, conjunctival fibrosis, subconjunctival fibrosis;
arthritis;
fibrotic pre-neoplastic and fibrotic neoplastic disease; and
fibrosis induced by chemical or environmental insult selected from cancer chemotherapy, pesticides, and radiation/cancer radiotherapy;
c) administering to a subject characterized as having fibroblast cells expressing pro-N-cadherin an anti-fibrotic therapeutic agent, wherein the anti-fibrotic therapeutic agent is the anti-pro-N-cadherin antibody 10A10.

2. The method of claim 1, wherein the sample comprises fibroblast cells, a stool sample, a blood sample, a tissue sample, and/or a blood fraction sample.

3. The method of claim 1, wherein the assaying comprises use of an antibody against pro-N-cadherin, and/or use of an immunoassay conducted with an antibody against pro-N-cadherin, and/or use of a microarray chip having one or more nucleic acid molecules that can hybridize under stringent conditions to a nucleic acid molecule encoding fibroblasts expressing pro-N-cadherin or having one or more polypeptides that can bind to fibroblasts expressing pro-N-cadherin.

4. The method of claim 1, further comprising administering to the subject one or more additional therapeutic agents selected from an anti-IL-13 agent, an anti-IL-4 agent, a combination anti-IL-13/anti-IL-4 agent, pirfenidone, an anti-LOXL2 antibody, N-acetylcysteine, an anti-TGF-β antibody, an anti-αvβ6 integrin antibody, an anti-CTGF antibody, an anti-CCL2 antibody, a somatostatin analog, an angiotension II inhibitor, carbon monoxide, thalidomide, tetrathiomolybdate, doxycycline, minocycline, and a tyrosine kinase inhibitor.

5. A method for treating, and/or ameliorating a condition associated with pathological fibroblast cells expressing pro-N-cadherin in a human subject, comprising administering to the human subject an anti-fibrotic therapeutic agent, wherein the anti-fibrotic therapeutic agent is capable of inhibiting expression and/or activity related to pro-N-cadherin expression and/or activity, wherein the anti-fibrotic therapeutic agent is the anti-pro-N-cadherin antibody 10A10, wherein the human subject is characterized as having fibroblast cells expressing pro-N-cadherin.

6. The method of claim 5, wherein the condition associated with pathological fibroblast cells expressing pro-N-cadherin is selected from fibrosis;

respiratory conditions selected from pulmonary fibrosis, cystic fibrosis, idiopathic pulmonary fibrosis, progressive massive fibrosis, scleroderma, obliterative bronchiolitis, Hermansky-Pudlak syndrome, asbestosis, silicosis, chronic pulmonary hypertension, AIDS associated pulmonary hypertension, sarcoidosis, tumor stroma in lung disease, and asthma;
chronic liver diseases selected from primary biliary cirrhosis (PBC), schistosomal liver disease, and liver cirrhosis;
cardiovascular conditions selected from hypertrophic cardiomyopathy, dilated cardiomyopathy (DCM), fibrosis of the atrium, atrial fibrillation, fibrosis of the ventricle, ventricular fibrillation, myocardial fibrosis, Brugada syndrome, myocarditis, endomyocardial fibrosis, myocardial infarction, fibrotic vascular disease, hypertensive heart disease, arrhythmogenic right ventricular cardiomyopathy (ARVC), tubulointerstitial and glomerular fibrosis, atherosclerosis, varicose veins, and cerebral infarcts;
neurological conditions selected from gliosis and Alzheimer's disease;
Duchenne muscular dystrophy (DMD);
Becker's muscular dystrophy (BMD);
gastrointestinal conditions selected from Crohn's disease, microscopic colitis and primary sclerosing cholangitis (PSC);
skin conditions selected from scleroderma, nephrogenic systemic fibrosis and cutis keloid;
arthrofibrosis;
Dupuytren's contracture;
mediastinal fibrosis;
retroperitoneal fibrosis;
myelofibrosis;
Peyronie's disease;
adhesive capsulitis;
kidney diseases selected from renal fibrosis, nephritic syndrome, Alport's syndrome, HIV associated nephropathy, polycystic kidney disease, Fabry's disease, diabetic nephropathy, chronic glomerulonephritis, and nephritis associated with systemic lupus;
progressive systemic sclerosis (PSS);
chronic graft versus host disease;
diseases of the eye selected from Grave's ophthalmopathy, epiretinal fibrosis, retinal fibrosis, subretinal fibrosis associated with macular degeneration, wet age-related macular degeneration (AMD), diabetic retinopathy, glaucoma, corneal fibrosis, post-surgical fibrosis of the posterior capsule following cataract surgery, post-surgical fibrosis of the bleb following trabeculectomy for glaucoma, conjunctival fibrosis, subconjunctival fibrosis;
arthritis;
fibrotic pre-neoplastic and fibrotic neoplastic disease; and
fibrosis induced by chemical or environmental insult selected from cancer chemotherapy, pesticides, and radiation/cancer radiotherapy.

7. The method of claim 5, further comprising administering to the subject one or more additional therapeutic agents selected from an anti-IL-13 agent, an anti-IL-4 agent, a combination anti-IL-13/anti-IL-4 agent, pirfenidone, an anti-LOXL2 antibody, N-acetylcysteine, an anti-TGF-β antibody, an anti-αvβ6 integrin antibody, an anti-CTGF antibody, an anti-CCL2 antibody, a somatostatin analog, an angiotension II inhibitor, carbon monoxide, thalidomide, tetrathiomolybdate, doxycycline, minocycline, and a tyrosine kinase inhibitor.

8. A method of treating fibrosis in a subject characterized as having fibroblast cells expressing pro-N-cadherin, the method comprising administering to the subject a therapeutically effective amount of a Pro-N-Cadherin inhibiting molecule such that the fibrosis is treated in the subject, wherein the inhibiting molecule is the monoclonal antibody 10A10.

* * * * *